(12) United States Patent
Molina

(10) Patent No.: US 11,712,199 B2
(45) Date of Patent: Aug. 1, 2023

(54) SYSTEM AND METHOD FOR OPTIMIZING SLEEP-RELATED PARAMETERS FOR COMPUTING A SLEEP SCORE

(71) Applicant: KONINKLIJKE PHILIPS N.V., Eindhoven (NL)

(72) Inventor: Gary Nelson Garcia Molina, Madison, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 670 days.

(21) Appl. No.: 16/724,572

(22) Filed: Dec. 23, 2019

(65) Prior Publication Data
US 2020/0205728 A1    Jul. 2, 2020

Related U.S. Application Data

(60) Provisional application No. 62/785,333, filed on Dec. 27, 2018.

(51) Int. Cl.
*A61B 5/00* (2006.01)
*G16H 50/30* (2018.01)
(Continued)

(52) U.S. Cl.
CPC ......... *A61B 5/4815* (2013.01); *A61M 21/00* (2013.01); *G06F 17/15* (2013.01); *G06F 17/16* (2013.01); *G16H 50/20* (2018.01); *G16H 50/30* (2018.01)

(58) Field of Classification Search
CPC ..... A61B 5/4815; A61B 5/0022; A61B 5/024; A61B 5/0816; A61B 5/11; A61B 5/318;
(Continued)

(56) References Cited

U.S. PATENT DOCUMENTS

| 6,120,441 A * | 9/2000 | Griebel | A61B 5/742 600/300 |
| 2004/0068199 A1* | 4/2004 | Echauz | G06K 9/627 600/544 |

(Continued)

OTHER PUBLICATIONS

International Search Report and Written Opinion dated Mar. 25, 2020 for International Application No. PCT/EP2019/086761 filed Dec. 20, 2019.
(Continued)

*Primary Examiner* — Sunita Reddy

(57) ABSTRACT

The present disclosure pertains to optimizing sleep score parameters. In one embodiment, a first set of vectors is obtained, where each vector includes parameter values of sleep-related parameters for calculating a sleep score. For each vector of the first set, a correlation value indicating a degree of a correlation between the vector and a user-indicated sleep score associated with a set of parameter values representative of a sleep metric of the user is determined. A second set of vectors is generated based on a first subset and a second subset of the first set of vectors satisfying a first and second criteria, respectively. A correlation value associated with each vector of the second set is determined. For each sleep-related parameter, a parameter value of a given vector of the second set is assigned based on the correlation values associated with the second set.

8 Claims, 17 Drawing Sheets

(51) Int. Cl.
  *G16H 50/20* (2018.01)
  *A61M 21/00* (2006.01)
  *G06F 17/15* (2006.01)
  *G06F 17/16* (2006.01)

(58) Field of Classification Search
  CPC ............ A61B 5/369; A61B 2562/0219; A61B 5/4809; A61B 5/4812; A61B 5/7246; A61M 21/00; A61M 2021/0022; A61M 2021/0027; A61M 2021/0044; A61M 2021/0066; A61M 2021/0083; A61M 2205/332; A61M 2205/3553; A61M 2205/3584; A61M 2205/3592; A61M 2205/505; A61M 2205/52; A61M 2209/088; A61M 2230/06; A61M 2230/10; A61M 2230/42; A61M 2230/63; A61M 21/02; G06F 17/15; G06F 17/16; G16H 50/20; G16H 50/30; G16H 40/67
  USPC ...................................... 600/26–28
  See application file for complete search history.

(56) References Cited

U.S. PATENT DOCUMENTS

| | | | | |
|---|---|---|---|---|
| 2004/0087878 | A1* | 5/2004 | Krausman | A61B 5/4815 600/587 |
| 2005/0042589 | A1* | 2/2005 | Hatlestad | A61B 5/4818 434/262 |
| 2005/0197590 | A1* | 9/2005 | Osorio | A61B 5/4094 600/544 |
| 2005/0209511 | A1* | 9/2005 | Heruth | A61N 1/36135 600/587 |
| 2007/0287930 | A1* | 12/2007 | Sutton | A61M 21/00 600/544 |
| 2010/0099954 | A1* | 4/2010 | Dickinson | G09B 19/00 600/300 |
| 2010/0197996 | A1* | 8/2010 | Cornel | A61M 21/00 600/28 |
| 2014/0076318 | A1 | 3/2014 | Flower | |
| 2016/0045035 | A1* | 2/2016 | Van Erlach | A61B 5/0036 700/279 |
| 2018/0229040 | A1 | 8/2018 | Srivastava | |
| 2019/0247650 | A1* | 8/2019 | Tran | A61N 1/3704 |

OTHER PUBLICATIONS

Ohayon, M.M. et al., 2004. Meta-analysis of quantitative sleep parameters from childhood to old age in healthy individuals: developing normative sleep values across the human lifespan. Sleep, 27(7), pp. 1255-1273.

Whitley, D., 1994. A genetic algorithm tutorial. Statistics and Computing, 4(2), pp. 65-85.

* cited by examiner

| 1300 | | |
|---|---|---|
| 2001_PSG08_20160713 | 1302 | |
| | 100 | |
| 1304 — Total sleep time | -72 | 223.5 minutes |
| 1306 — Sleep routine | -5 | 86.22 minutes |
| 1308 — Time to fall asleep | 0 | 11.6 minutes |
| 1310 — Time spent awake | -10 | 136 minutes |
| 1312 — Number of interruptions | -6 | 3 |
| 1314 — Duration N3 sleep | 0 | 80 minutes |
| | 7 | |
| 1316 — Base score | 46 | |
| | 0 | |
| 1318 — Therapy points | 5 | |
| | 7 | |
| 1320 — Healthy sleep score | 51 | |

FIG. 13

| | Factor | Value of parameters to build the initial population |
|---|---|---|
| 206 — | Total sleep time | 1406 — 1. [300, 360, 420] minutes |
| | | 1408 — 2. [60, 120, 180] minutes |
| | | 1410 — 3. [40, 50] points |
| 208 — | Wake after sleep onset | 1412 — 4. [5, 10] points |
| 210 — | Sleep onset latency | 1414 — 5. [5, 10] points |
| 212 — | Sleep disruptions | 1416 — 6. [10, 20] points |
| | | 1418 — 7. [5, 10] interruptions |
| 214 — | N3 duration | 1420 — 8. [10, 20] points |
| 216 — | REM duration | 1422 — 9. [10, 20] points |
| 218 — | Regularity | 1424 — 10. [40, 60] minutes |
| | | 1426 — 11. [5, 10] points |
| 220 — | Bonus | 1428 — 12. [20, 30] points |

FIG. 14

SYSTEM AND METHOD FOR OPTIMIZING SLEEP-RELATED PARAMETERS FOR COMPUTING A SLEEP SCORE

CROSS-REFERENCE TO PRIOR APPLICATIONS

This application claims the benefit of U.S. Provisional Application No. 62/785,333, filed on 27 Dec. 2018. This application is hereby incorporated by reference herein.

BACKGROUND

1. Field

The present disclosure pertains to a system and method for facilitating sleep-related parameter optimization for computing a sleep score.

2. Description of the Related Art

Systems for monitoring sleep are known. Techniques for computing a sleep score are known. A sleep score can be computed via a subtractive approach where points are subtracted from an initial value based on sleep-related factors computed using sleep data from an individual's sleep session. The sleep-related factors are determined using initialized sleep-related parameter values. To be meaningful to the individual, the sleep score should clearly and simply convey how the sleep score was determined. Additionally, the sleep score should be well correlated with the individual's subjective analysis of the sleep session. Current systems used to determine sleep scores, however, can be unclear and may not accurately reflect the individual's subjective sleep analysis. The present disclosure overcomes deficiencies in such systems.

SUMMARY

Accordingly, one or more aspects of the present disclosure relate to a method for optimizing sleep score parameters. The method includes obtaining a first set of vectors, where each vector of the first set of vectors includes parameter values of sleep-related parameters for calculating a sleep score. For each vector of the first set of vectors, a correlation value associated with the vector is determined, the correlation value for the vector indicating an amount of a correlation between the vector and a user-indicated sleep score associated with a set of parameter values representative of a sleep metric of the user. The method includes generating a second set of vectors based on (i) a first subset of the first set of vectors having correlation values that satisfy a first criterion, and (ii) a second subset of the first set of vectors having correlation values that satisfy a second criterion. For each vector of the second set of vectors, a correlation value associated with the vector is determined such that the correlation value for the vector indicates an amount of correlation between the vector and the user-indicated sleep score. For each parameter of the sleep-related parameters, a parameter value of a given vector of the second set of vectors is assigned to the parameter of the sleep-related parameters based on the correlation values associated with the second set of vectors.

Another aspect of the present disclosure relates to a system for optimizing sleep score parameters. The system includes memory and one or more processors configured by machine-readable instruction stored by the memory to obtain a first set of vectors, where each vector of the first set of vectors includes parameter values of sleep-related parameters for calculating a sleep score. For each vector of the first set of vectors, a correlation value associated with the vector is determined, the correlation value for the vector indicating an amount of a correlation between the vector and a user-indicated sleep score associated with a set of parameter values representative of a sleep metric of the user. The one or more processors are configured by the machine-readable instructions to generate a second set of vectors based on (i) a first subset of the first set of vectors having correlation values that satisfy a first criterion, and (ii) a second subset of the first set of vectors having correlation values that satisfy a second criterion. For each vector of the second set of vectors, a correlation value associated with the vector is determined such that the correlation value for the vector indicates an amount of correlation between the vector and the user-indicated sleep score. The one or more processors are configured by the machine-readable instructions to assign, for each parameter of the sleep-related parameters, a parameter value of a given vector of the second set of vectors to the parameter of the sleep-related parameter based on the correlation values associated with the second set of vectors.

Yet another aspect of the present disclosure relates to a system for optimizing sleep score parameters. The system includes means for obtaining a first set of vectors, wherein each vector of the first set of vectors includes parameter values of sleep-related parameters for calculating a sleep score; means for determining, for each vector of the first set of vectors, a correlation value associated with the vector, the correlation value for the vector indicating a degree of a correlation between the vector and a user-indicated sleep score associated with a set of parameter values representative of a sleep metric of the user; means for generating a second set of vectors based on (i) a first subset of the first set of vectors having correlation values that satisfy a first criterion, and (ii) a second subset of the first set of vectors having correlation values that satisfy a second criterion; means for determining, for each vector of the second set of vectors, a correlation value associated with the vector such that the correlation value for the vector indicates an amount of a correlation between the vector the user-indicated sleep score; and means for assigning, for each parameter of the sleep-related parameters, a parameter value of a given vector of the second set of vectors to the parameter of the sleep-related parameters based on the correlation values associated with the second set of vectors.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

BRIEF DESCRIPTION OF THE DRAWINGS

FIG. 13 is an illustrative diagram of an example interface displaying a sleep score and the computed values for a variety of sleep-related parameters used to determine the sleep score, in accordance with various embodiments;

FIG. 14 is an illustrative diagram of the various sleep factors and the values of each sleep-related parameter used to generate an initial set of chromosome vectors, in accordance with various embodiments;

DETAILED DESCRIPTION OF EXEMPLARY EMBODIMENTS

As used herein, the singular form of "a", "an", and "the" include plural references unless the context clearly dictates otherwise. As used herein, the term "or" means "and/or" unless the context clearly dictates otherwise. As employed herein, the term "number" shall mean one or an integer greater than one (i.e., a plurality).

Figure 1A:
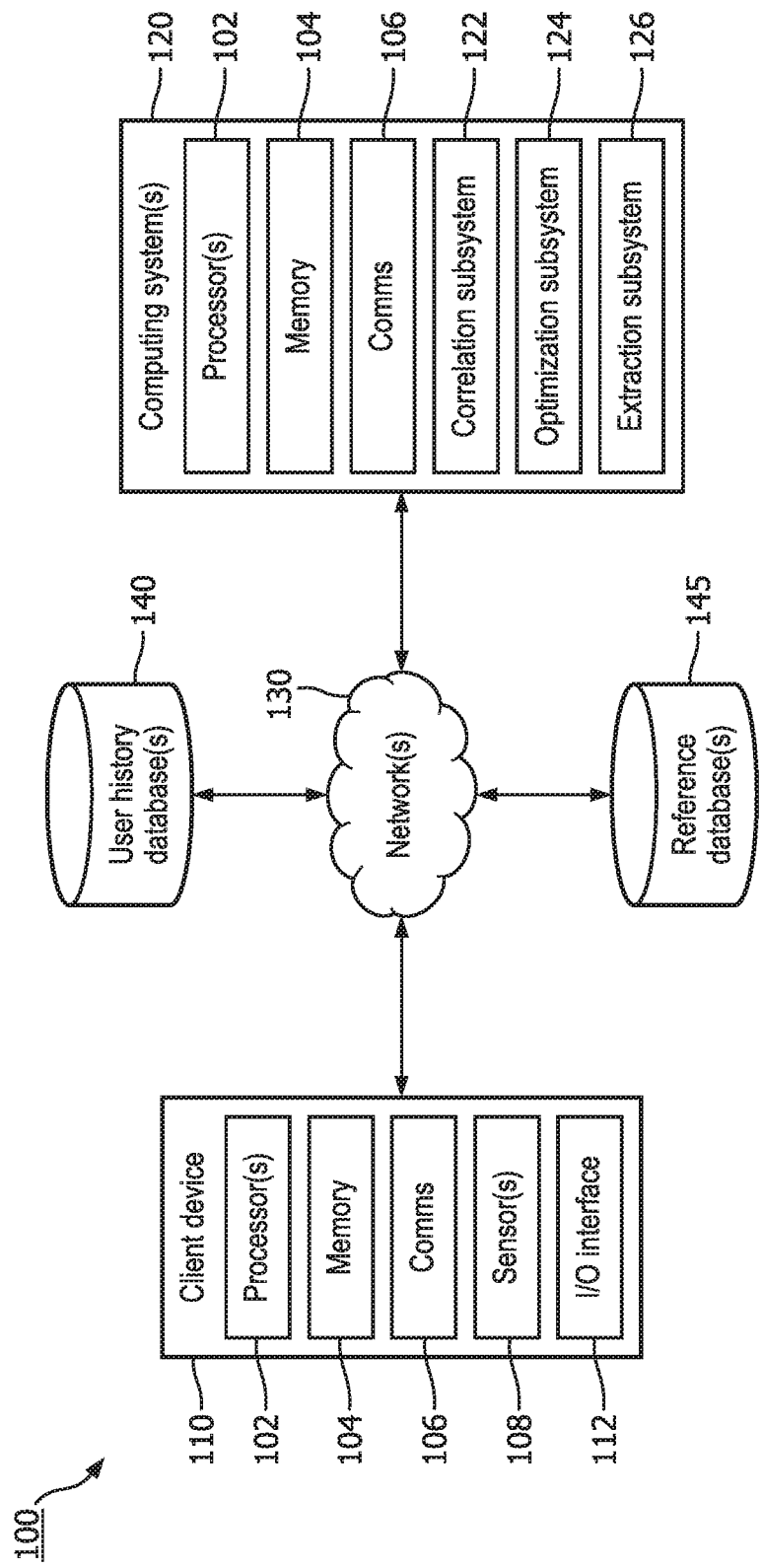
FIG. 1A is a schematic illustration of an exemplary system configured to facilitate sleep-related parameter optimization, in accordance with various embodiments.

FIG. 1A is a schematic illustration of an exemplary system configured to facilitate sleep-related parameter optimization, in accordance with various embodiments. System 100, in one embodiment, includes a first client device 110, one or more computing systems 120, a user history database or databases 140, and a reference database or databases 145. Each of client devices 110, computing system(s) 120, user history database(s) 140, and reference database(s) 145 may communicate with one another via one or more network(s) 130. For example, client device 110 and computing system(s) 120 may communicate over an intranet and/or the Internet.

In some embodiments, client device 110 or computing systems 120 are configured to monitor activity of a user and store inputs detected by one or more sensors 108. Sensor(s) 108 may include any suitable sensor capable of measuring one or more parameters of an associated user. For example, sensor(s) 108 may include one or more accelerometers, one or more gyroscopes, one or more pulse rate monitors, one or more breath monitoring devices, and/or one or more electroencephalography ("EEG") devices. In one embodiment, sensor(s) 108 are configured to take measurements at pre-defined temporal intervals. For instance, sensor(s) 108 may be configured (e.g., by processor(s) 102 using instructions stored by memory 104) to take a "sample" measurement at a particular time interval (e.g., every second). A sampling rate—how often sensor(s) 108 take a measurement—is configurable by client device 110 and depends on a type of sensor(s) 108 as well as a type of the measurement. In one embodiment, the sampling rate is dynamic and may be set based on a type of sensor(s) 108 and a measurement type. In one embodiment, the sampling rate is set by a user operating client device 110, where the user manually selects the sampling rate based on the user's determination of what is appropriate for the type of sensor(s) 108. For example, if sensor(s) 108 is a pulse rate monitor, then client device 110 may configure the sampling rate to be 10 kHz. As another example, if sensor(s) 108 is an accelerometer, client device 110 may configure the sampling rate to be 1,000 kHz.

Client device 110, in one embodiment, includes any suitable type of electronic device such as, and without limitation, desktop computers, mobile computers (e.g., laptops, ultrabooks, etc.), mobile phones, smart phones, tablets, personal digital assistants ("PDAs"), and/or wearable devices (e.g., watches, pins/broaches, headphones, etc.). Furthermore, in the illustrative embodiment, client device 110 includes one or more processors 102, memory 104, communications circuitry 106 ("comms"), and an input/output ("I/O") interface 112.

Processor(s) 102 includes any suitable processing circuitry capable of controlling operations and functionality of client device 110, as well as facilitating communications between various components within client device 110. In one embodiment, processor(s) 102 may include a central processing unit ("CPU"), a graphic processing unit ("GPU"), one or more microprocessors, a digital signal processor, or any other type of processor, or any combination thereof. In another embodiment, the functionality of processor(s) 102 is performed by one or more hardware logic components including, but not limited to, field-programmable gate arrays ("FPGA"), application specific integrated circuits ("ASICs"), application-specific standard products ("ASSPs"), system-on-chip systems ("SOCs"), and/or complex programmable logic devices ("CPLDs"). Furthermore, each of processor(s) 102 is capable of including its own local memory, which may store program systems, program data, and/or one or more operating systems. However, processor(s) 102 are capable of running an operating system ("OS") for client device 110, and/or one or more firmware applications, media applications, and/or applications resident thereon.

Memory 104, in one embodiment, includes one or more types of storage mediums such as any volatile or non-volatile memory, or any removable or non-removable memory implemented in any suitable manner to store data for client device 110. For example, information may be stored using computer-readable instructions, data structures, and/or program systems. Various types of storage/memory may include, but are not limited to, hard drives, solid state drives, flash memory, permanent memory (e.g., ROM), electronically erasable programmable read-only memory ("EEPROM"), CD-ROM, digital versatile disk ("DVD") or other optical storage medium, magnetic cassettes, magnetic tape, magnetic disk storage or other magnetic storage devices, RAID storage systems, or any other storage type, or any combination thereof. Furthermore, memory 104 may be implemented as computer-readable storage media ("CRSM"), which may be any available physical media accessible by processor(s) 102 to execute one or more instructions stored within memory 104. For example, memory 104 may store machine-readable instructions that, upon being executed, cause processor(s) 102 to perform various operations. In one embodiment, machine-readable instructions associated with executing one or more applications (e.g., sleep tracking application, heart rate monitor applications, etc.) using processor(s) 102 are stored in memory 104.

Communications circuitry 106, in one embodiment, includes any circuitry allowing or enabling one or more components of client device 110 to communicate with one another, and/or with one or more additional devices, servers, and/or systems (e.g., computing system(s) 120, user history database 140, reference database 145). As an illustrative example, data obtained by sensor(s) 108 may be transmitted over a network 130, such as the Internet, to computing system(s) 120 using any number of communications protocols. For example, network(s) 130 are capable of being accessed using Transfer Control Protocol and Internet Protocol ("TCP/IP") (e.g., any of the protocols used in each of the TCP/IP layers), Hypertext Transfer Protocol ("HTTP"), WebRTC, SIP, and wireless application protocol ("WAP"), are some of the various types of protocols that may be used to facilitate communications between client device 110 and computing system(s) 120. In one embodiment, client device 110 and computing system(s) 120 communicate with one another via a web browser using HTTP. Various additional communication protocols used to facilitate communications between one or more devices of system 100 include, but not limited to, Wi-Fi (e.g., 802.11 protocol), Bluetooth, radio frequency systems (e.g., 900 MHz, 1.4 GHz, and 5.6 GHz communication systems), cellular networks (e.g., GSM, AMPS, GPRS, CDMA, EV-DO, EDGE, 3GSM, DECT, IS-136/TDMA, iDen, LTE or any other suitable cellular network protocol), infrared, BitTorrent, FTP, RTP, RTSP, SSH, and/or VOIP. Communications circuitry 106 is capable of using one or more communications protocols, such as any of the previously mentioned exemplary communications protocols. In one embodiment, client device 110 includes one or more antennas to facilitate wireless communications with a network, e.g., network(s) 130, using various wireless technologies (e.g., Wi-Fi, Bluetooth, radiofrequency, etc.). In yet another embodiment, client device 110 includes one or more universal serial bus ("USB") ports, one or more Ethernet or broadband ports, and/or any other type of hardwire access port so that communications circuitry 106 allows client device 110 to communicate with one or more communications networks, e.g., network(s) 130.

I/O interface 112 is configured to receive input data from one or more external sources or as a result of one or more inputs from, e.g., a user. I/O interface 112 is also configured to output data in various data formats such as, and without limitation, audio, video, images, text files, e-mails, etc. Various example I/O interfaces include one or more microphones or other audio input devices, one or more speakers or other audio output devices, one or more input mechanisms (e.g., buttons, knobs, switches, etc.), one or more cameras or other image capture devices, and/or one or more display screens. For example, client device 110 may include a display screen of any suitable size and/or shape. Various types of displays include, but are not limited to, liquid crystal displays ("LCD"), monochrome displays, color graphics adapter ("CGA") displays, enhanced graphics adapter ("EGA") displays, variable graphics array ("VGA") display, or any other type of display, or any combination thereof. In one embodiment, client device 110 includes a touch screen, such as a touch screen including capacitive sensing panels capable of recognizing touch inputs thereon. For instance, a touch screen may be a projected capacitive touch ("PCT") screen, where the PCT screen includes one or more row traces and/or driving line traces, as well as one or more column traces and/or sensing lines.

In one embodiment, as a user sleeps, client device 110 monitors sleep activity of the user. Sleep activity may include motion of the user, a pulse rate of the user, a breath rate of the user, brainwave activity of the user, or any combination thereof. As an example, client device 110 may be a wearable sleep tracking device configured to monitor movement of the user during a sleep session. In one embodiment, client device 110 is configured to send data associated with a sleep session of the user to computing system(s) 120 via network(s) 130. In one embodiment, client device 110 provides the data to computing system(s) 120 at an end of the sleep session. Alternatively, or additionally, client device 110 is configured to send the data to computing system(s) 120 periodically (e.g., every 5-10 minutes).

In one embodiment, client device 110 is further configured to provide an input mechanism for a user to input a sleep rating for a given sleep session. For example, a graphical user interface ("GUI") may be displayed via a display screen (e.g., I/O interface 112), and the GUI may indicate a computed sleep score for a given sleep session. In one embodiment, the GUI further includes an option for the user to input a "rating" for the sleep session. For example, the user may be able to type in a numerical value, e.g., an integer between 0-100, to reflect the user's subjective rating of their sleep session. The user-provided sleep score, which may also be referred to herein as a "user-indicated sleep score," is provided to computing system(s) 120. Additionally, or alternatively, the user-indicated sleep score is provided to user history database(s) 140 to be stored with computed sleep score for the sleep session of the user. The user-indicated sleep score may also include one or more other subjective ratings provided by the user with respect to the sleep session of the user or to a sleep score calculated from objective factors.

Computing system(s) 120, in one embodiment, includes a correlation subsystem 122, an optimization subsystem 124, and an extraction subsystem 126. Each of subsystems 122-126 is configured to perform one or more operations associated with computing a user sleep score based on data obtained from client device 110, such as performing correlations between user-indicated sleep scores and calculated sleep scores, optimizing sleep-related parameter values for computing sleep scores, and computing the sleep scores based on user sleep data and optimized (or to be optimized) sleep-related parameter values. In one embodiment, computing system(s) 120 includes one or more instances of processor(s) 102, memory 104, and communications circuitry 104, which are similar in functionality those of client device 110. In one embodiment, subsystems 122-126 reside on separate computing systems 120 (e.g., a distribution computing system) or on a single computing system 120.

In one embodiment, each subsystem includes one or more computer programs that, when executed, cause one or more functionalities of the subsystems to be performed. For instance, computing system 120 is configured to determine a sleep score of a user for a particular sleep session or collection of sleep sessions. For example, one or more computer programs stored within memory of computer system 120 may cause one or more sleep score deductions and/or sleep score bonuses to be computed, and these deduction(s) and/or bonus(es) are used to compute a particular sleep score for a given sleep session. Computing system(s) 120 is configured to receive the data associated with a sleep session from client device 110 and determine one or more sleep metrics associated with the sleep session. For example, sleep architecture, sleep continuity, a sleep onset, and/or a sleep wakeup time are all exemplary types of metrics capable of being determined for a particular sleep session. The sleep architecture, for instance, includes a duration of each sleep stage (e.g., N3, N2, N1, REM, etc.), a latency of each sleep stage, and/or a survival curve of each sleep stage.

User history database 140 stores information associated with a user's sleep session history. For example, user history database 140 may store information indicating a time or times of sleep onset for a particular user, a time or times of sleep wakeup, and the like. In one embodiment, historical sleep information for a particular user is stored by user history database 140, and is accessible by computing system(s) 120 via network 130. In one embodiment, user history database 140 includes discrete memory blocks with which information associated with a particular user's sleep history is stored. For example, each user of computing system 120 may have their own sleep information stored within a portion of user history database 140. The stored sleep information includes computed sleep scores for a particular user, as well as user-indicated sleep scores provided by the user. In one embodiment, the computed sleep score and the user-indicated sleep score are stored together, or are linked based on an identifier associated with the particular sleep session they correspond to. In one embodiment, correlations between the user-indicated sleep score and the computed sleep score for each sleep session over a period of time (e.g., one week, one month, etc.) is determined by correlation subsystem 122, which is described in greater detail below with reference to FIGS. 2 and 15.

Reference database 145 stores information associated with data pertaining to the user associated with client device 110. For example, reference database 145 may store information indicating an age, gender, geographic localization, and/or chronotype of a user. In one embodiment, parameter values for computing sleep-related parameters for the user are stored in reference database. For example, reference database 145 may store optimized values for each sleep-related parameter, which may then be used to compute subsequent sleep scores for that user. Optimizing parameter values for sleep-related parameters is performed in one embodiment by optimization subsystem 124, which is described in greater detail below with reference to FIGS. 2, 15, and 16.

In one embodiment, extraction subsystem 126 is configured to extract the optimized parameter values for each sleep-related parameter based on an output from optimization system, as described in greater detail below with reference to FIGS. 2, 15, and 16. For example, optimization subsystem 124 may determine a sleep score associated with sleep score vector that is determined to be most correlated with user-indicated sleep score information provided by the user and stored in user history database(s) 140. Based on the sleep score vector, extraction subsystem 126 is configured to extract the optimized parameter values for the sleep-related parameters. The optimized sleep-related parameters are then stored, for example, in reference database 145.

In one embodiment, computing system(s) 120 is configured to determine a number of deductions associated with a particular sleep session, and an amount (e.g., a severity/magnitude) of each deduction. To do this, a comparison between the sleep metrics associated with a particular sleep session and the reference sleep metrics (e.g., user history sleep information, reference sleep information) that have previously been obtained may be performed. Computing system(s) 120 is configured to use these comparisons to determine one or more immediate values related to the first sleep session. For example, the immediate values may include one or more deductions to be applied to a sleep score.

Although the aforementioned and foregoing are described in the context of computing system(s) 120 performing analysis with respect to user sleep session data, persons of ordinary skill in the art will recognize that client device 110, in one embodiment, is configured to perform some or all of the same analysis. For instance, memory 104 of client device 110 may store machine-readable instructions for executing one or more processes (e.g., process 1500 of FIG. 15, process 1600 of FIG. 16) to optimize sleep-related parameter values. Alternatively, or additionally, memory 104 of client device 110 is capable of storing machine-readable instructions for executing one or more processes for determining sleep score deductions, sleep score bonuses, and applying the sleep score deductions and sleep score bonuses to an initial sleep score value to determine a sleep score for a given sleep session.

In one embodiment, seven different types of sleep deductions are used. In this embodiment, the deductions correspond to one or more of a total sleep time ("TST"), a total time spent awake between a sleep onset time and a sleep offset time (e.g., a wake after sleep onset ("WASO")), a number of sleep disruptions that occurred during a sleep session (e.g., a period of wakefulness exceeding a threshold amount of time between sleep onset and sleep offset), a sleep routine that depends on a regularity of sleep onset and wakeup times, a sleep onset latency ("SOL") (e.g., a duration of time to sleep onset), a deduction based on N3 sleep duration (e.g., "deep sleep"), and a deduction based on REM sleep duration. Persons of ordinary skill in the art will recognize that the aforementioned list of sleep deduction types is merely exemplary, and more or fewer sleep deductions types may be employed. Furthermore, a bonus is applied for certain positive sleep behaviors that are exhibited by the user or the effect of an intervention (e.g. auditory stimulation to enhance sleep slow-waves), determined based on the user's age and slow-wave brain activity detected.

In an exemplary embodiment, computing system(s) 120 starts with an initial sleep session score. For each deduction determined for a particular sleep session, the deduction is added to the initial sleep session score. In one embodiment, the deductions are negative (e.g., <0). Alternatively, for example, the deductions may be subtracted from the initial sleep session score, and therefore the deductions are positive (e.g., >0). After applying (e.g., adding/subtracting) each deduction to the initial sleep session score, a new sleep session score is obtained. In one embodiment, the new sleep session score is provided to the user via I/O interface 112. For example, if I/O component 112 includes a display device, computing system(s) 120 may cause the new sleep session score to be displayed by a graphical user interface via the display device. The sleep score, in one embodiment, is presented as an integer value. For example, the sleep score is an integer between 0 and 100. In one embodiment, in addition to the new sleep session score, the magnitude of the sleep factors associated with the computed sleep session score are displayed to the user. For example, an interface is displayed on the display screen indicating a number of times the user was awake, and further how the number of times the user was awake related to a particular parameter value for a particular sleep-related parameter used to compute the current sleep sessions score, as illustrated in FIG. 13.

In one embodiment, in addition to providing an interface for displaying the computed sleep score, a user may input a rating for a sleep session. The user-indicated rating, or user-indicated sleep score, allows the user to input their own rating to indicate how well he/she believed their sleep session was, i.e., a quality of his/her sleep session. The computed sleep score should be close to the user-indicated sleep score for the user to have confidence that the computed sleep score accurately reflects their sleep quality. For instance, if a computed sleep score is 80, and the user-indicated sleep score is also 80, then the calculated sleep score metric accurately reflect the user's own assessment of his/her sleep quality. However, if the computed sleep score is 80 and the user-indicated sleep score is 20, then the calculated sleep score metric does not accurately reflect the user's sleep quality. Furthermore, a user may consistently rate their sleep with a particular variance or bias with respect to the computed sleep score. For example, if the user consistently provides a user-indicated sleep score that is 5-10 points less than or greater than the computed sleep score, the "offset" or "bias" should also be considered to promote more accurate sleep score computations.

In one embodiment, client device 110 or another device in system 100 includes an intervention unit. The intervention causes a sleep intervention to be output/performed to promote quality sleep. Such sleep intervention components include, but not limited to, one or more auditory stimulation devices, one or more visual stimulation devices, one or more haptic stimulation devices, one or more closed-loop sleep induction devices, one or more smart wakeup devices, and the like. In one example embodiment, the intervention unit causes a temperature of a local environment with which the user is located to be adjusted. For example, the intervention unit may cause a thermostat in a user's household to raise or lower the temperature in order to promote quality sleep.

In one embodiment, one or more sleep interventions that occurred during a sleep session are determined based on the user data that has been obtained. For instance, if one or more sleep interventions occurred during a first sleep session, then the user data obtained by sensor(s) 108 may indicate this and therefore computing system(s) 120 may identify the intervention(s) within the user data. Each of the sleep interventions may be applied to the initial sleep session score (or the sleep session score including the deductions, as described above), to generate a new sleep session score. For example, the sleep interventions may be represented as a bonus applied to an initial sleep score to increase the sleep session score value in a manner akin to the sleep deductions being applied to the initial sleep score to decrease the sleep session score value.

As seen from Equation 1, the sleep session score value is capable of being determined where:

$$\text{Sleep\_Session\_Score} = \text{Initial\_Sleep\_Score} + \Sigma\text{Sleep\_Deductions} + \Sigma\text{Sleep\_Interventions} \qquad \text{Equation 1.}$$

In Equation 1, Initial_Sleep_Score is an exemplary initial sleep session score, such as the number 100, $\Sigma$ Sleep_Deductions is a sum of all of the sleep deductions (e.g., where each deduction is negative or zero in value), and $\Sigma$ Sleep_Interventions is a sum of all of the bonuses awarded based on the provided sleep interventions (e.g., where the bonus is positive in value).

Figure 1B:
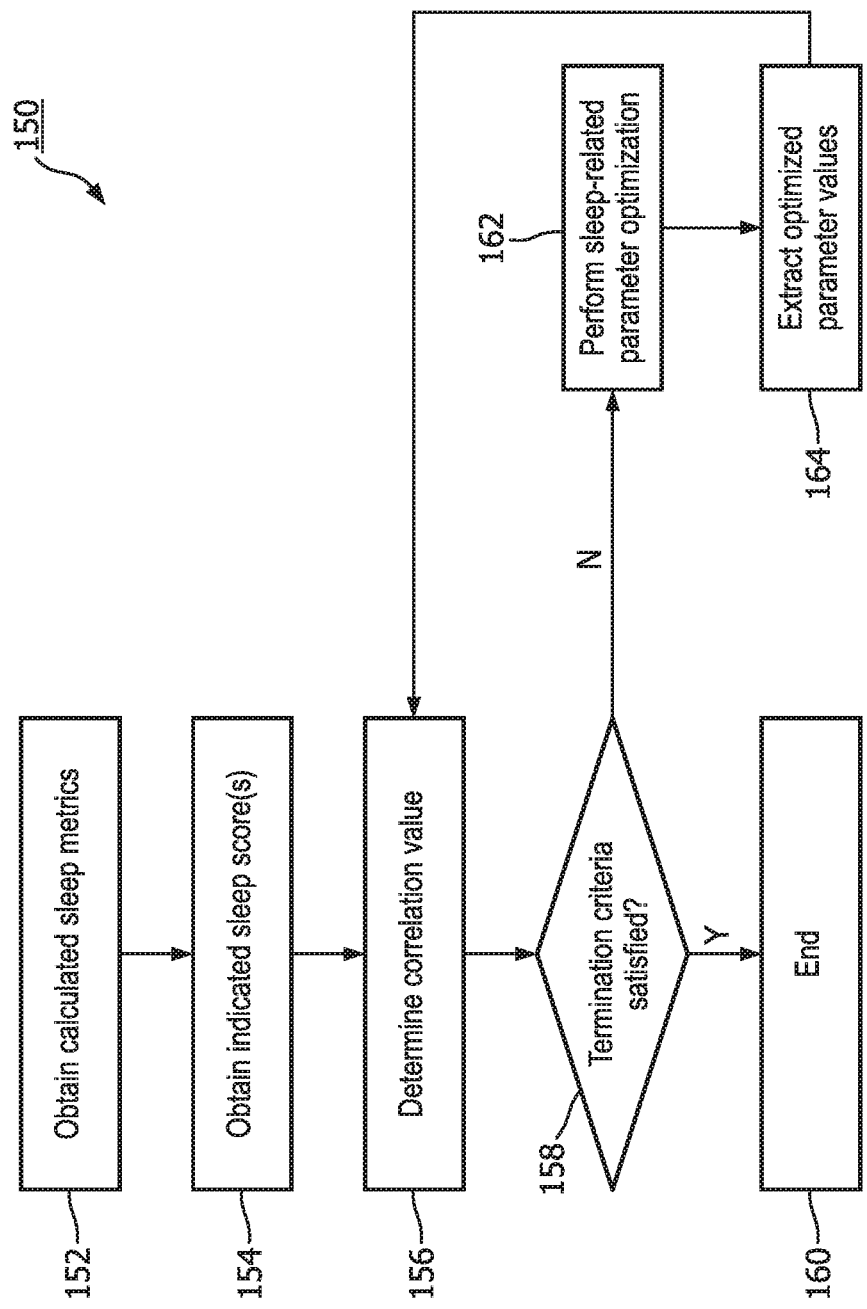
FIG. 1B is an illustrative flowchart of an exemplary process for determining whether sleep-related parameter optimization is to be performed, in accordance with various embodiments.

FIG. 1B is an illustrative flowchart of process 150 for determining whether sleep-related parameter optimization is to be performed, in accordance with various embodiments. In one embodiment, process 150 of FIG. 1B begins at operation 152. At operation 152, calculated sleep metrics for a user are obtained. In one embodiment, each calculated sleep metric is a sleep score computed for a given sleep session of a user based on data received from client device 110 during that sleep session. In one embodiment, a plurality of sleep metrics (e.g., seven sleep scores, thirty sleep scores, etc.) are obtained at operation 152. In one embodiment, computing system 120 is configured to receive the calculated sleep metrics from user history database 140. For instance, at periodic intervals, e.g., weekly, monthly, annually, etc., computing system 120 requests a particular user's sleep metric data from user history database 140. Alternatively, or additionally, computing system 120 is configured to request a user's sleep metric data from user history database 140 upon a triggering event, such as a request from a user operating client device 110 to review his/her sleep metrics, a request from a medical practitioner to review the user's sleep metrics, or both. In one embodiment, a user's sleep metric data is obtained from client device 110. For example, computing system 120 may be configured to request sleep metric data for a particular user, which may be stored in memory 104 of client device 110. In one embodiment, the user's sleep metric data used to determine an average sleep score of the user for a particular amount of time. For example, an average calculated sleep score may be determined based on e.g., a week, a month, a year, of calculated sleep scores for a user.

At operation 154, one or more user-indicated sleep scores are obtained. The user-indicated sleep scores, which are also referred to herein as "user-indicated sleep scores," indicate a user's subjective rating of their sleep session or sleep sessions. In one embodiment, a user is presented with an interface via client device 110 that allows for a user-indicated sleep score to be input. For example, after a sleep session has ended, a user may input a rating for the quality of their sleep, which may be stored within memory 104, communicated to computing system 120, and/or stored within user history database 140. The user-indicated sleep score can be an integer-based value between 0 and 100, for example, however other ranges, e.g., between 0-1.0, 0-10, etc., may be used. In one embodiment, the user-indicated sleep scores include a plurality of user-indicated sleep scores provided by the user for a particular amount of time. For example, the obtained user-indicated sleep scores may be for one week of sleep sessions (e.g., seven scores). In one embodiment, upon receiving the user-indicated sleep scores for a given amount of time, an average user-indicated sleep score for that amount of time is determined. For example, computing system 120 may compute the average user-indicated sleep score from a user for a given amount of time. In one embodiment, the amount of time used to determine the average user-indicated sleep score is equal to the amount of time used to determine the average calculated sleep score. For example, if a week of calculated sleep scores for a user is used, then a week of user-indicated sleep scores, e.g., seven user-indicated sleep scores, from that same week will be used.

At operation 156, a correlation between the calculated sleep scores and the user-indicated sleep score is determined. In one embodiment, correlation subsystem 122 is configured to determine a correlation value for the user-indicated sleep scores and the calculated sleep scores for a given data set. For instance, computing system(s) 120 receives data including the user-indicated sleep scores and the calculated sleep scores for a given amount of time from memory 104, user history database(s) 140, or both, and computes the correlation value based on the received data.

In one embodiment, correlation subsystem 122 determines the correlation based on an average calculated sleep score and an average user-indicated sleep score for a given amount of time with which data was collected, e.g., one week. The correlation value measures how closely related two variable are. In the illustrative embodiment, the two variables are the user-indicated sleep score and the calculated sleep score. In one embodiment, the correlation value is computed using a Pearson's correlation technique. Using the Pearson's correlation, a correlation between the user-indicated sleep score and the calculated sleep score is determined based on differences between the average calculated sleep score and each calculated sleep score for a given data set (e.g., one week's worth of calculated sleep scores), differences between the average user-indicated sleep score and each user-indicated sleep score for the given data set (e.g., one week's worth of user-indicated sleep scores), and standard deviations for both the calculated sleep score and the user-indicated sleep score. Equation 2 is a formulaic representation of the Pearson's correlation value for the aforementioned embodiment:

$$r = \frac{\sum_{i=1}^{n}(SubSleepScore_i - \overline{SubSleepScore})(CalSleepScore_i - \overline{CalSleepScore})}{(n-1)\sigma_{SubSleep}\sigma_{CalSleep}}.$$

Equation 2

In Equation 2, r is the correlation value computed using the Pearson's correlation, $SubSleepScore_i$ is the i-th user-indicated sleep score for a given data set, $\overline{SubSleepScore}$ is the average user-indicated sleep score for the given data set, $CalSleepScore_i$ is the i-th calculated sleep score for the given data set, $\overline{CalSleepScore}$ is the average calculated sleep score for the given data set, and $\sigma_{SubSleep}$ and $\sigma_{CalSleep}$ are the standard deviation for the user-indicated sleep score and the calculated sleep score, respectively. Although the aforementioned describes the correlation value estimated using Pearson's correlation formula, other correlation coefficients can be used, such as an adjusted correlation coefficient, a weighted correlation coefficient, and Spearman correlation coefficient.

At operation 158, correlation subsystem 122 determines whether the determined correlation value satisfies termination criteria. In one embodiment, the termination criteria may be a threshold value with which correlation is measured. In one embodiment, the termination criteria include a first threshold value with which correlation is measured, e.g., a lower bound threshold, and a second threshold value with which correlation is measured, e.g., an upper bound threshold. The termination criteria is stored in one or more of memory 104 of computing system 120, reference database 145, and user history database 140. The greater the correlation value, the more closely correlated the user-indicated sleep score and the calculated sleep score are to one another. As an example, the threshold value for the termination criteria may be equal to 0.3. Thus, if the determined correlation value is less than 0.3, then the user-indicated sleep score and the calculated sleep scores are not well correlated. However, if the determined correlation value is less than or equal to 0.3, then the user-indicated sleep score and the calculated sleep score are correlated. The threshold value of 0.3 is exemplary, and different threshold may be used, e.g., 0.2-0.5.

Furthermore, in one embodiment, differences between each sleep session's user-indicated sleep score and calculated sleep score are determined by correlation subsystem 122, and the differences are used to compute a similarity between the user-indicated sleep score and the calculated sleep score. An average of each difference between the user-indicated sleep score and the calculated sleep score is then compared to the termination criteria to determine whether the scores are correlated.

If, at operation 158, correlation subsystem 122 determines that the correlation value for the given data set satisfies the termination criteria, then process 150 proceeds to operation 160. At operation 160, correlation subsystem 122 determines that process 150 is to end as the user-indicated sleep score and the calculated sleep score have been determined to be well correlated, indicating that the sleep-related parameters used to compute the calculated sleep scores accurately reflect the user's subjective analysis of his/her sleep sessions. Thus, the sleep-related parameters, in this example, do not need adjustment.

However, if at operation 158 correlation subsystem 122 determines that the correlation value for the given data set does not satisfy the termination criteria, then process 150 proceeds to operation 162. At operation 162, sleep-related parameter optimization is performed. In one embodiment, optimization subsystem 124 performs sleep-related parameter optimization, as described below with respect to FIGS. 2 and 14-16. At operation 164, optimized parameter values for each sleep-related parameters used to compute the sleep score for a user (e.g., Equation 1) are extracted. In one embodiment, extraction subsystem 126 performs the extraction of the optimized sleep-related parameter values. After operation 162, process 150 returns to step 156, where a new correlation value is computed based on sleep scores calculated using the optimized sleep-related parameters extracted at step 164. In one embodiment, the new correlation value is computed for a new data set of calculated sleep scores (e.g., calculated using the new sleep-related parameter values) and user-indicated sleep scores. Alternatively, the previously obtained calculated sleep scores are recomputed, and the correlation value is recalculated to determine how well the previously calculated sleep scores and the previously obtained user-indicated sleep scores are correlated with one another.

Figure 2:
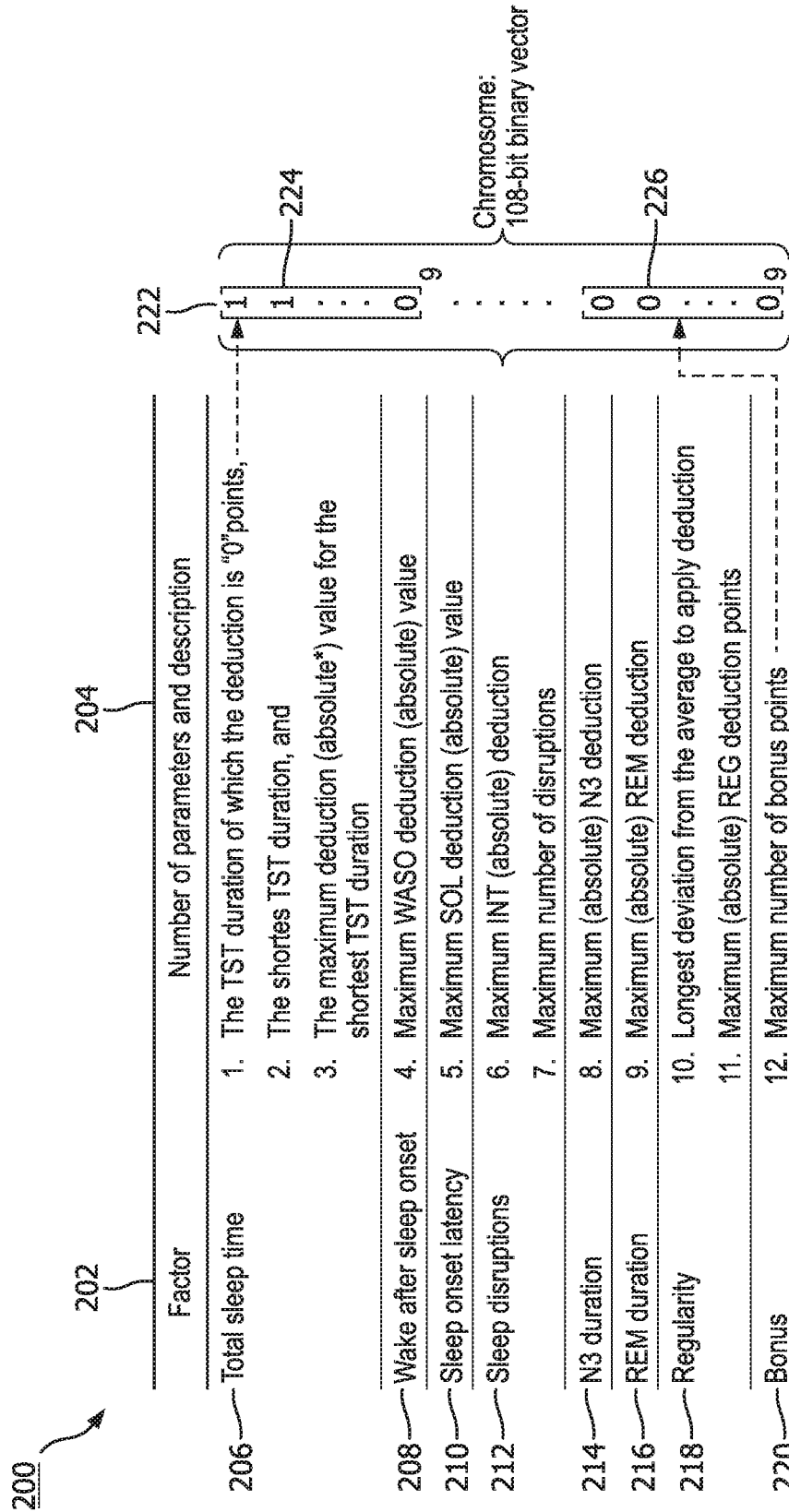
FIG. 2 is an illustrative diagram of a chromosome vector generated based on a plurality of sleep-related parameters used for various sleep factors to calculate a sleep score, in accordance with various embodiments.

FIG. 2 is an illustrative diagram of a chromosome vector generated based on a plurality of sleep-related parameters used for various sleep factors to calculate a sleep score, in accordance with various embodiments. In FIG. 2, factors used to compute a sleep score for a user are presented in a first column 202 of a table 200. In the illustrative embodiment, the factors displayed within column 202 include a total sleep time ("TST") factor 206, a wake after sleep onset ("WASO") factor 208, a sleep onset latency ("SOL") factor 210, a sleep disruption factor 212, an N3 duration factor 214, a REM duration factor 216, a regularity factor 218, and a bonus factor 220. Each of factors 206-220 contribute to a calculated sleep score for a user. In one embodiment, each of factors 206-218 are subtracted from an initial sleep score (e.g., 100), while bonus factor 220 is added to the initial sleep score, as detailed in Equation 1 above.

In second column 204 of table 200, sleep-related parameters associated with each of factors 206-220 are presented. Different factors include a different number of parameters. For example, TST factor 206 includes three parameters; WASO factor 208, SOL factor 210, N3 duration factor 214, REM duration factor 216, and bonus factor 220 each include one parameter; and sleep durations factor 212 and regularity factor 218 each include two parameters. In the illustrative embodiment, each parameter is quantified using nine-bit binary vector. Thus, the twelve sleep-related parameters for determining sleep scores, when concatenated, result in a 108-bit binary vector 222. In one embodiment, 108-bit binary vector 222 is utilized for optimizing the correlation between the calculated sleep scores and the user-indicated sleep scores. Prior to describing the process for optimizing each of the twelve parameters, details related to each of the sleep-related parameters and its effect on computing sleep scores is described.

Figure 3:
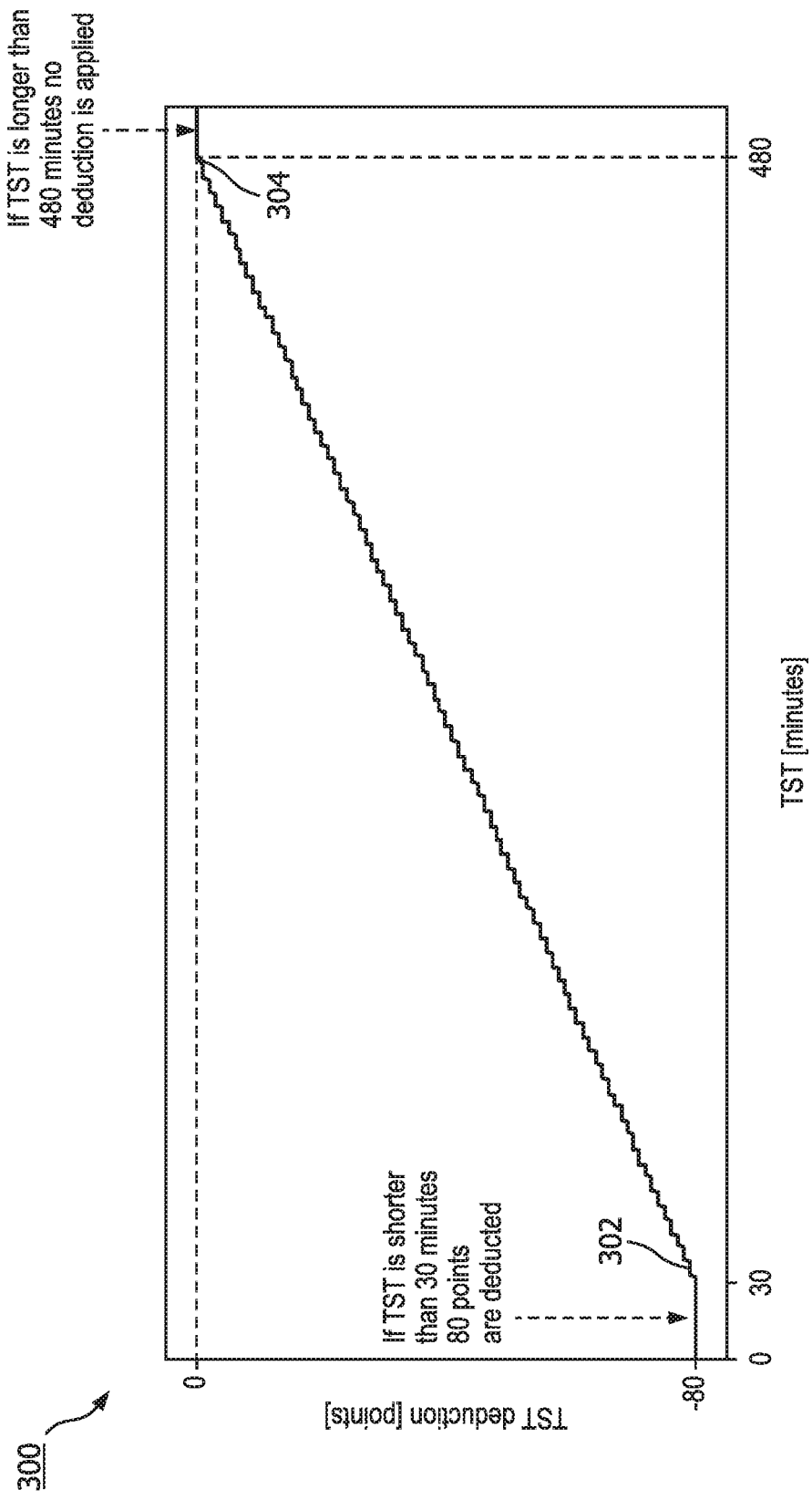
FIG. 3 is an illustrative diagram describing a relationship between total sleep time and a corresponding sleep score point deduction, in accordance with various embodiments.

FIG. 3 is an illustrative diagram describing a relationship between total sleep time and a corresponding sleep score point deduction, in accordance with various embodiments. In FIG. 3, an exemplary graph 300 is shown describing the relationship between a total sleep time ("TST") for a user and a sleep score point deduction value. In one embodiment, the TST may be an amount of time a user is determined to be asleep. TST includes all accumulated sleep (e.g., NREM and REM) periods within a given sleep session. In one embodiment, a determination of whether a user is asleep or awake is based on data obtained from sensor(s) 108 of client device 110. For example, motion data indicated periods of non-movement for greater than a threshold amount of time (e.g., 20 minutes, 60 minutes, etc.) may indicate that a user is asleep. As another example, brainwave activity indicating sleep-related brainwaves may indicate that a user is asleep.

After determining, based on the data obtained from sensor(s) 108, a total amount of time that the user has slept during a sleep session, e.g., TST, computing system(s) 120 determines whether the TST is greater than (or equal to) a predefined threshold value 304 for TST. If so, then computing system(s) 120 is configured to apply a TST point deduction of zero points. For example, threshold value 304 is 480 minutes, then an amount of deductions for TST may be zero. In one embodiment, threshold value 304 may be one of the sleep-related parameters described above. This parameter can be optimized based on data obtained from a plurality of sleep sessions.

If the TST is less than threshold value 304 for TST, computing system(s) 120 is configured to apply a particular deduction. This deduction, for instance, is associated with a total duration of the TST and thus is configured such that, depending on the total duration of the TST, the deduction differs. As seen in graph 300, for TST durations that are less than or equal to a first threshold 302, a first deduction is applied by computing system(s) 120. In one embodiment, first threshold 302 represents a maximum point deduction allowable for the sleep score based on TST. For example, if the amount of time of sleep is less than 30 minutes, computing system(s) 120 applies a maximum point deduction. In one embodiment, threshold 302 and the maximum point deduction based on TST correspond sleep-related parameters, which can be optimized for a particular user based on data obtained from a plurality of sleep sessions. If a TST duration is greater than or equal to first threshold 302 but less than a second threshold 304, then a deduction applied is dependent, i.e., proportional, on a functional relationship between TST and a point deduction amount. As an example, this deduction is linearly related to the TST duration if the TST duration is less than threshold 304 and greater than threshold 302.

Figure 4:
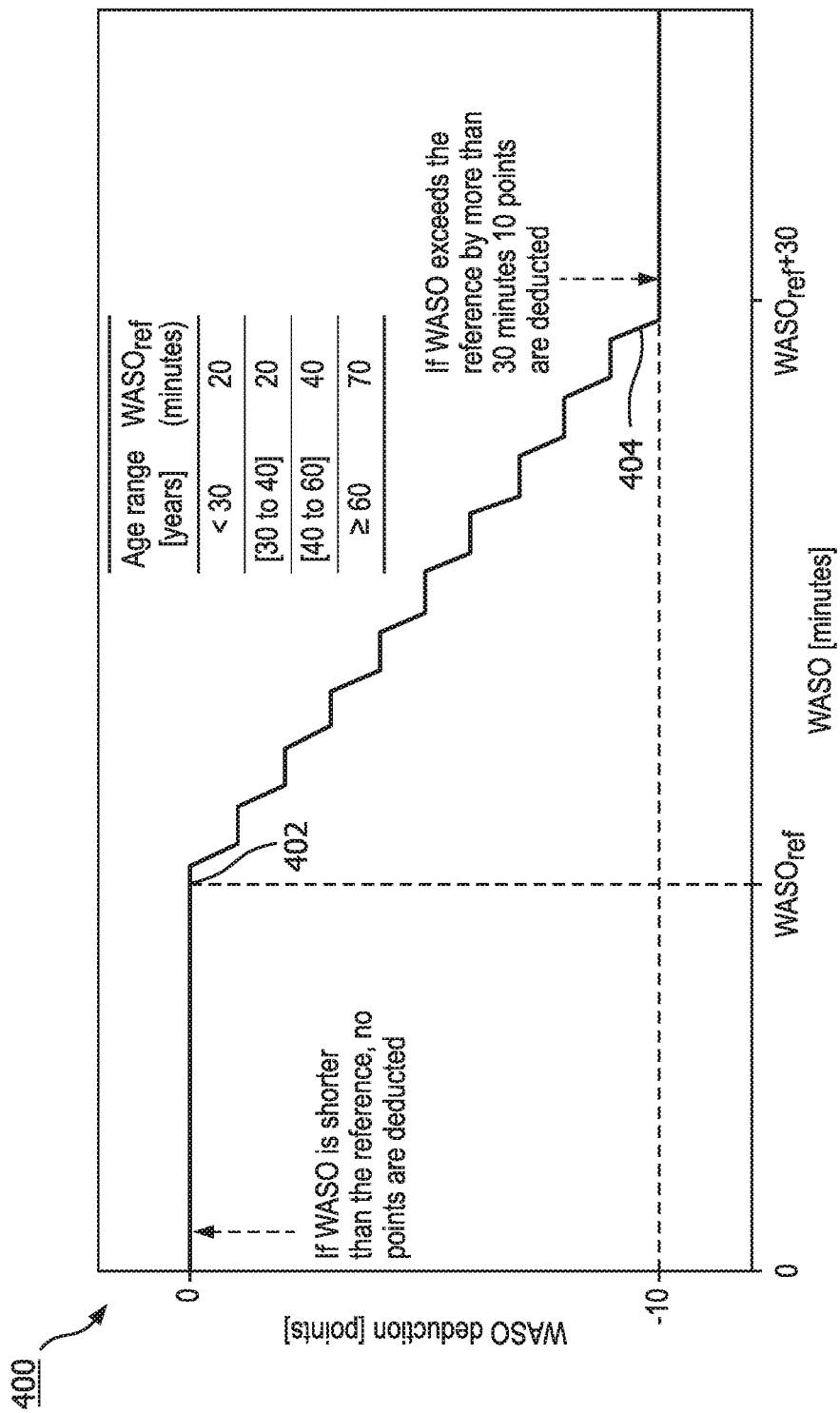
FIG. 4 is an illustrative diagram describing a relationship between a number of times a user wakes up after sleep onset and a corresponding sleep score point deduction, in accordance with various embodiments.

FIG. 4 is an illustrative diagram describing a relationship between a number of wake after sleep onset time and a corresponding sleep score point deduction, in accordance with various embodiments. FIG. 4 includes an illustrative graph 400 used for determining a total time spent awake deduction. Wake after sleep onset ("WASO") is an accumulation of periods of detected wakefulness between sleep onset and sleep offset. The WASO is related to WASO factor 208, which contributes to a calculated sleep score for a given sleep session. WASO includes not only time awake, but also micro-arousals, and more generally any amount of time that a user spends awake during a given sleep session (e.g., user activity detected by sensor(s) 108 exceeding a threshold value) after sleep onset is identified.

In one embodiment, a deduction based on WASO depends on an age of the user, as seen below with reference to Table 1. The age of the user indicates a reference value, $WASO_{ref}$, which corresponds to a maximum WASO duration before deductions are to be applied.

TABLE 1

| Age Range | $WASO_{ref}$ [minutes] |
|---|---|
| <30 | 20 |
| [30 to 40[ | 20 |
| [40 to 60[ | 40 |
| ≥60 | 70 |

In one embodiment, $WASO_{ref}$ is illustrated as value 402 in graph 400. The deduction is minimal if the WASO is less than or equal to threshold 402. In the illustrative embodiment, a deduction of zero is applied if the WASO amount of time is less than first threshold 402. The deduction is maximal a detected WASO is equal to or exceeds threshold 404. In one embodiment, threshold 404 may be $WASO_{ref}$ plus a certain amount of time (e.g., 30 minutes). If the WASO is greater than threshold 402 and less than threshold 404, then the deduction for WASO factor 208 is determined based on the proportionality defined within FIG. 4. In one embodiment, the maximum deduction for WASO factor 208 is a sleep-related parameter that is capable of being optimized for a user based on data obtained from a plurality of sleep sessions.

Figure 5:
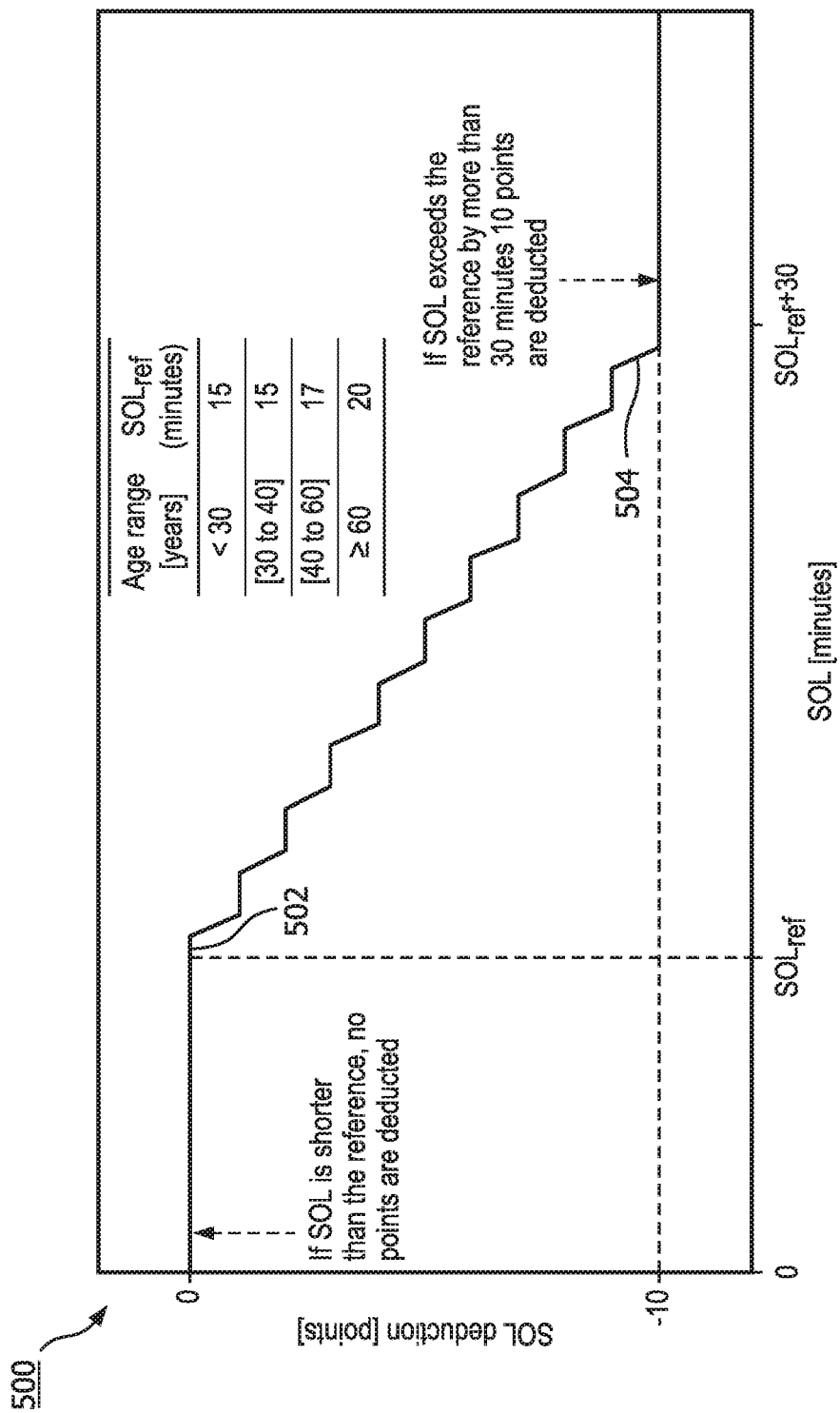
FIG. 5 is an illustrative diagram describing a relationship between a sleep onset latency time and a corresponding sleep score point deduction, in accordance with various embodiments.

FIG. 5 is an illustrative diagram describing a relationship between sleep onset latency time and a corresponding sleep score point deduction, in accordance with various embodiments. FIG. 5 includes an illustrative graph 500 describing a relationship between sleep onset latency SOL and sleep score point deductions for SOL factor 210. SOL refers to an amount of time with which it takes for a user to fall asleep. A deduction associated with SOL, in one embodiment, depends on an age range associated with the user. Table 2 includes various exemplary values that are applicable for $SOL_{ref}$ depending on an age of a user. In one embodiment, reference database 145 stores values for $SOL_{ref}$ included within Table 2. For instance, various age-based SOL deductions are stored by reference database 150, and these values are accessible by computing system 120 to determine a sleep score for a user's sleep session.

TABLE 2

| Age Range | $SOL_{ref}$ [minutes] |
|---|---|
| <30 | 15 |
| [30 to 40[ | 15 |
| [40 to 60[ | 17 |
| ≥60 | 20 |

In one embodiment, the age range indicates a SOL reference duration, e.g., $SOL_{ref}$, such that if the detected SOL is less than $SOL_{ref}$ no deductions are applied, whereas if the detected SOL exceeds $SOL_{ref}$ by a certain amount of time (e.g., 30 minutes), then the maximum deduction is applied. In one embodiment, first threshold 502 is $SOL_{ref}$ such that if the detected SOL, e.g., based on data obtained from sensor(s) 108 of client device 110, is less than or equal to threshold 502, SOL factor 210 is equal to zero points (e.g., zero points are deducted from the initial sleep score). In one embodiment, if the detected SOL is greater than or equal to second threshold 504, then a maximum amount of points are deducted for SOL factor 210. In one embodiment, the maximum amount of points deducted is a parameter that is optimized for a user based on data obtained from a plurality of sleep sessions. If the detected SOL is less than threshold 504 and greater than threshold 502, then the deductions applied for SOL factor 210 are proportional to the detected SOL time, as seen within graph 500.

Figure 6:
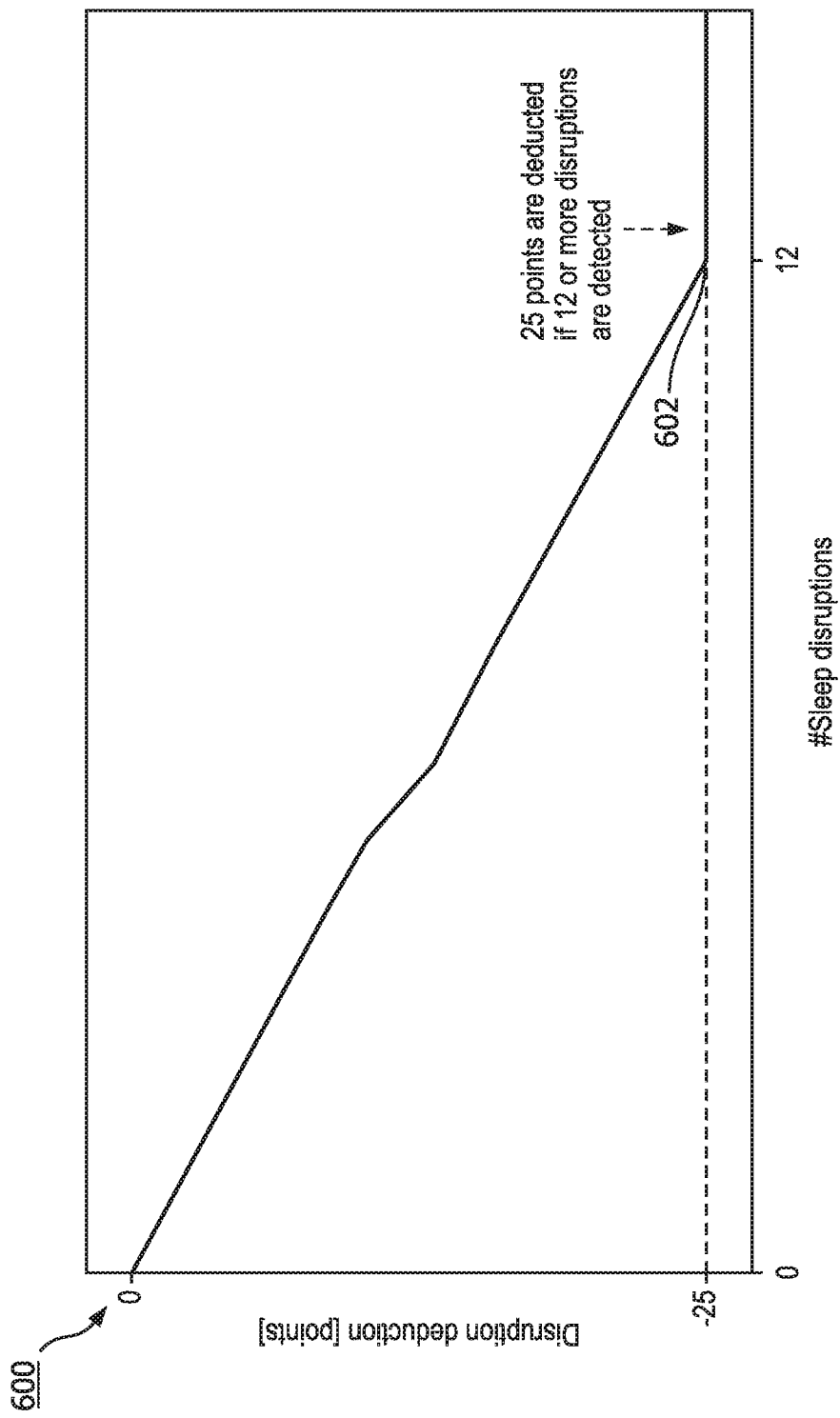
FIG. 6 is an illustrative diagram describing a relationship between a number of sleep disruptions and a corresponding sleep score point deduction, in accordance with various embodiments.

FIG. 6 is an illustrative diagram describing a relationship between a number of sleep disruptions and a corresponding sleep score point deduction, in accordance with various embodiments. FIG. 6 includes an illustrative graph 600 indicating a relationship between deduction to a sleep session score value based on a number of sleep disruptions detected, relating to sleep disruption factor 212. In one embodiment, a sleep disruption is characterized as a period of wakefulness between a sleep on-set and a sleep off-set that is at least a certain amount of time in duration. For example, a period of wakefulness in excess of five minutes may be deemed a sleep disruption.

In one embodiment, deductions for sleep disruption factor 212 are applied based on a number of sleep disruptions that occur during a sleep session. A largest amount of deduction is applied if the number of sleep disruptions is equal to or greater than a threshold number of disruptions 602. If no disruptions are detected during a sleep session, then a deduction of 0, or no deduction, is applied. For a number of disruptions greater than zero but less than threshold number 602, a deduction amount is proportional to the number of disruptions as described in graph 600. In one embodiment, a maximum deduction amount is 25 points for 12 or more sleep distributions detected. In one embodiment, the maximum deduction for number of sleep disruptions is a sleep-related parameter that can be optimized for a user based on data obtained for a plurality of sleep sessions. Furthermore, in one embodiment, the maximum number of disruptions is a sleep-related parameter that can be optimized based on data obtained from the plurality of sleep sessions.

Figure 7:
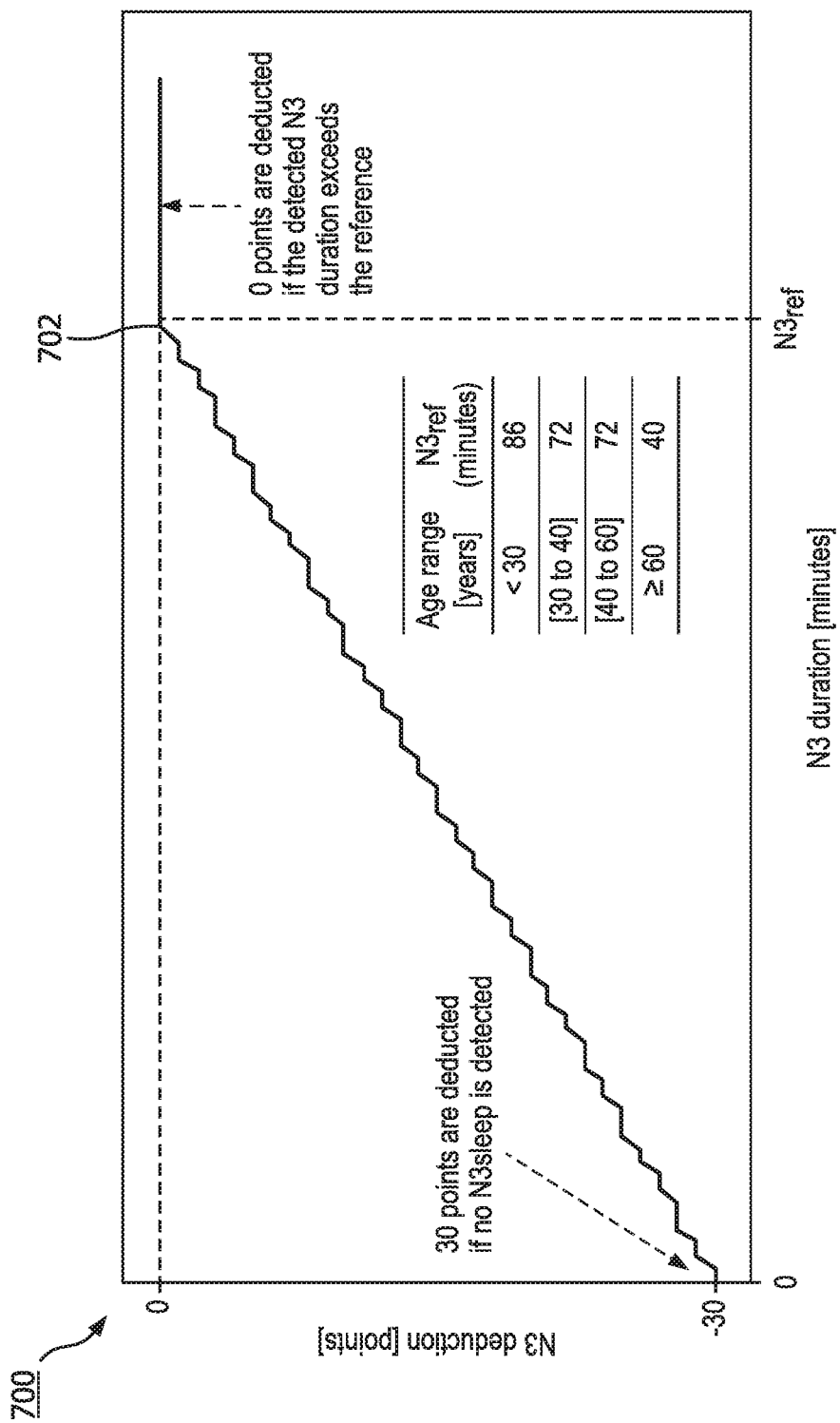
FIG. 7 is an illustrative diagram describing a relationship between an N3 sleep duration and a corresponding sleep score point deduction, in accordance with various embodiments.

FIG. 7 is an illustrative diagram describing a relationship between an N3 sleep duration and a corresponding sleep score point deduction, in accordance with various embodiments. FIG. 7 includes an illustrative graph 700 applicable to determining a sleep session score value based on a duration of N3 sleep, relating to N3 duration factor 214. In one embodiment, the deduction associated with N3 sleep duration factor 214, also referred to as a duration of deep sleep or slow-wave sleep, considers the recuperative value of sleep as being primarily driven by the presence of deep sleep. If, during a given sleep session, the duration of deep sleep, e.g., N3 sleep, does not meet an age matched reference threshold 702 (e.g., N3.sub.ref), as seen below by Table 3, a deduction is applied. The deduction is proportional (e.g., linearly proportional), in one embodiment, to a duration of the N3 deep sleep for that particular sleep session, which is determined based on data obtained from sensor(s) 108 of client device 110. In one embodiment, the maximum amount of deduction, e.g., maximum number of points, that can be applied when computing a sleep score is for an N3 sleep duration of approximately 0 minutes. If, however, the detected duration of N3 sleep is greater than or equal to age matched reference threshold 702, no deductions are applied. In one embodiment, the maximum deduction for N3 duration factor 214 is a sleep-related parameter that can be optimized based on data obtained from the plurality of sleep sessions.

TABLE 3

| Age Range | $N3_{ref}$ [minutes] |
|---|---|
| <30 | 86 |
| [30 to 40[ | 72 |
| [40 to 60[ | 72 |
| ≥60 | 40 |

Figure 8:
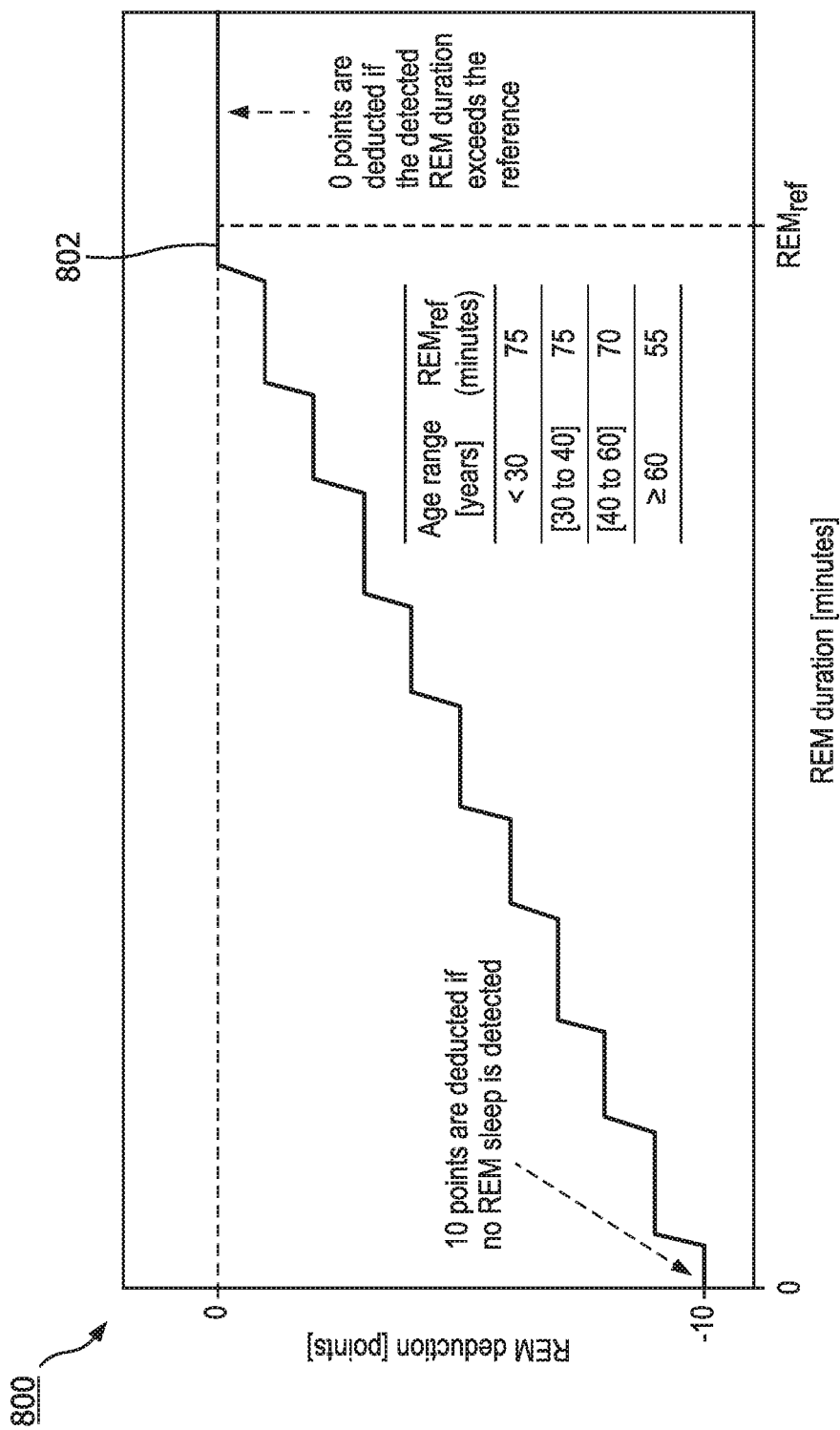
FIG. 8 is an illustrative diagram describing a relationship between a REM sleep duration and a corresponding sleep score point deduction, in accordance with various embodiments.

FIG. 8 is an illustrative diagram describing a relationship between a REM sleep duration and a corresponding sleep score point deduction, in accordance with various embodiments. FIG. 8 includes an illustrative graph 800 of a deduction applicable to calculating a sleep session score value based on a duration of REM sleep, relating to REM duration factor 216. If, during a given sleep session, the duration of REM sleep does not meet an age matched reference threshold 802 (e.g., $REM_{ref}$), as seen below by Table 4, a deduction is applied. The deduction is proportional (e.g., linearly proportional), in one embodiment, to a duration of the REM deep sleep for that particular sleep session for a detected REM duration less than threshold 802 but greater than zero. In one embodiment, the REM duration is determined based on data obtained from sensor(s) 108 of client device 110. In one embodiment, the maximum amount of deduction, e.g., a maximum number of points, that can be applied when computing a sleep score is for a REM sleep duration of approximately 0 minutes. If, however, the detected duration of REM sleep is greater than or equal to age matched reference threshold 802, no deductions are applied. In one embodiment, the maximum deduction for REM factor 216 is a sleep-related parameter that can be optimized based on data obtained from the plurality of sleep sessions.

TABLE 4

| Age Range | REM$_{ref}$ [minutes] |
|---|---|
| <30 | 75 |
| [30 to 40[ | 75 |
| [40 to 60[ | 70 |
| ≥60 | 55 |

Figure 9:
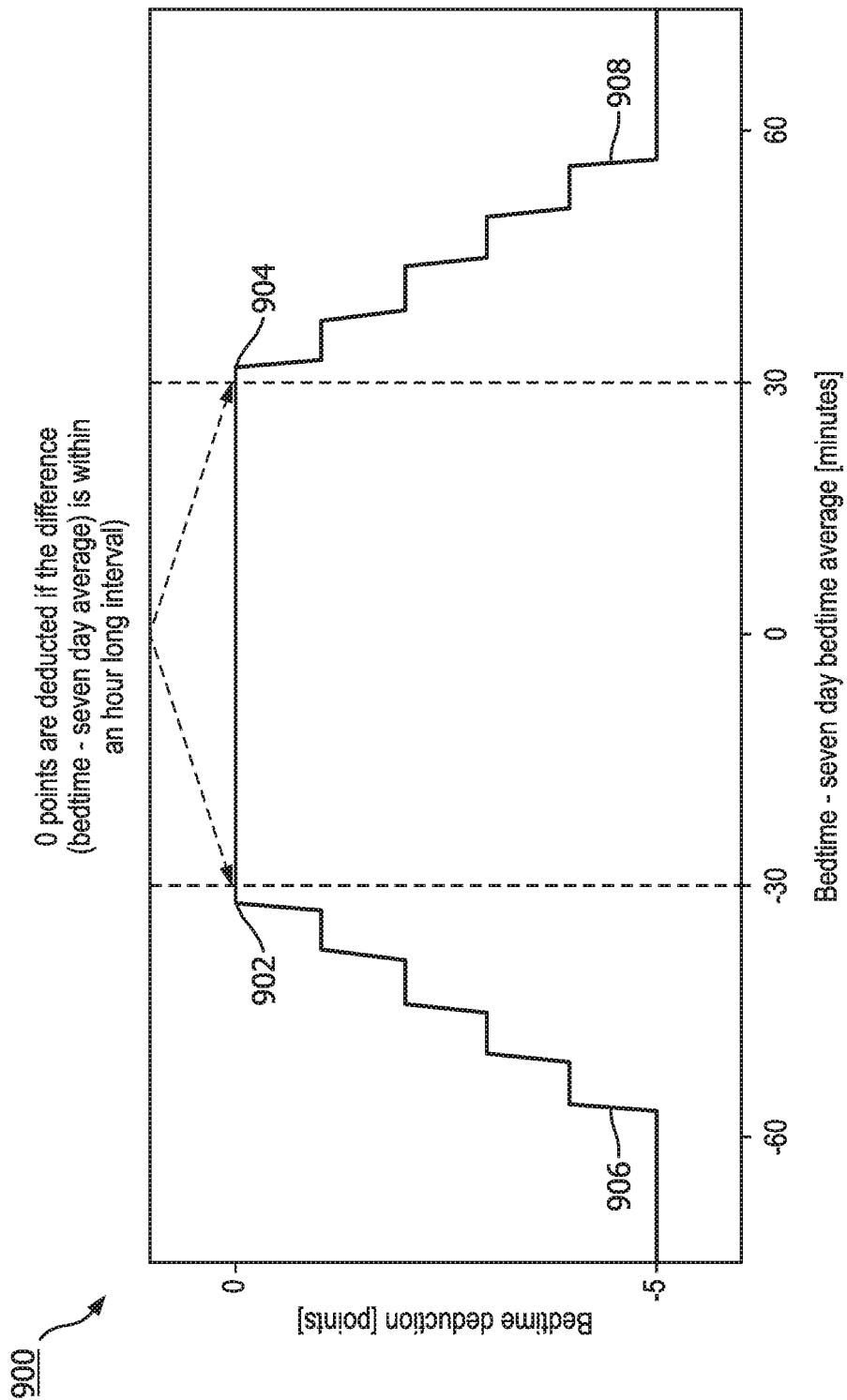
FIG. 9 is an illustrative diagram describing a relationship between a bedtime deviation and a corresponding sleep score point deduction, in accordance with various embodiments.

FIG. 9 is an illustrative diagram describing a relationship between a bedtime deviation and a corresponding sleep score point deduction, in accordance with various embodiments. FIG. 9 includes an illustrative graph 900 of deductions applicable for computing a sleep session score based on an amount of deviation from an average bedtime of the user, which relates to regularity factor 218. Regularity factor 218 relates to the idea of encouraging a user to have a regular bedtime routine. Therefore, if it is determined, based on data obtained from sensor(s) 108 of client device 110, that a user's bedtime (e.g., a time when the user goes to sleep) deviates from an average bedtime, a deduction is applied. In one embodiment, the average bedtime is determined based on a set of bedtimes for a given period of time. For example, the average bedtime may be computed based on seven days of bedtimes, however other amounts of time can be used.

In one embodiment, if a detected bedtime for a current sleep session is determined to be greater than or equal to a first threshold 902 and less than or equal to a second threshold, then a deduction of 0 points will be applied for regularity factor 218. As an example, an amount of time between first threshold 902 and second threshold 904 may be one hour (e.g., 60 minutes). If the deviation from the average bedtime for a given sleep session is less than threshold 902 or greater than threshold 904, then the deduction applied for factor 218 may be proportional to the deviation amount, as illustrated in graph 900. In one embodiment, a maximum deduction amount may be applied if the deviation is less than or equal to threshold 906 or greater than or equal to threshold 908. For example, if the deviation from the average bedtime exceeds one hour (e.g., 60 minutes) from the average bedtime, then the maximum deduction amount may be applied for factor 218. In one embodiment, the maximum deduction applied for regularity factor 218 is a sleep-related parameter that can be optimized for a user based on data obtained from the plurality of sleep sessions. Furthermore, in one embodiment, the longest deviation from the average bedtime with which the maximum deduction for factor 218 is to be applied is also a sleep-related parameter that can be optimized for a user based on data obtained from the plurality of sleep sessions.

Figure 10:
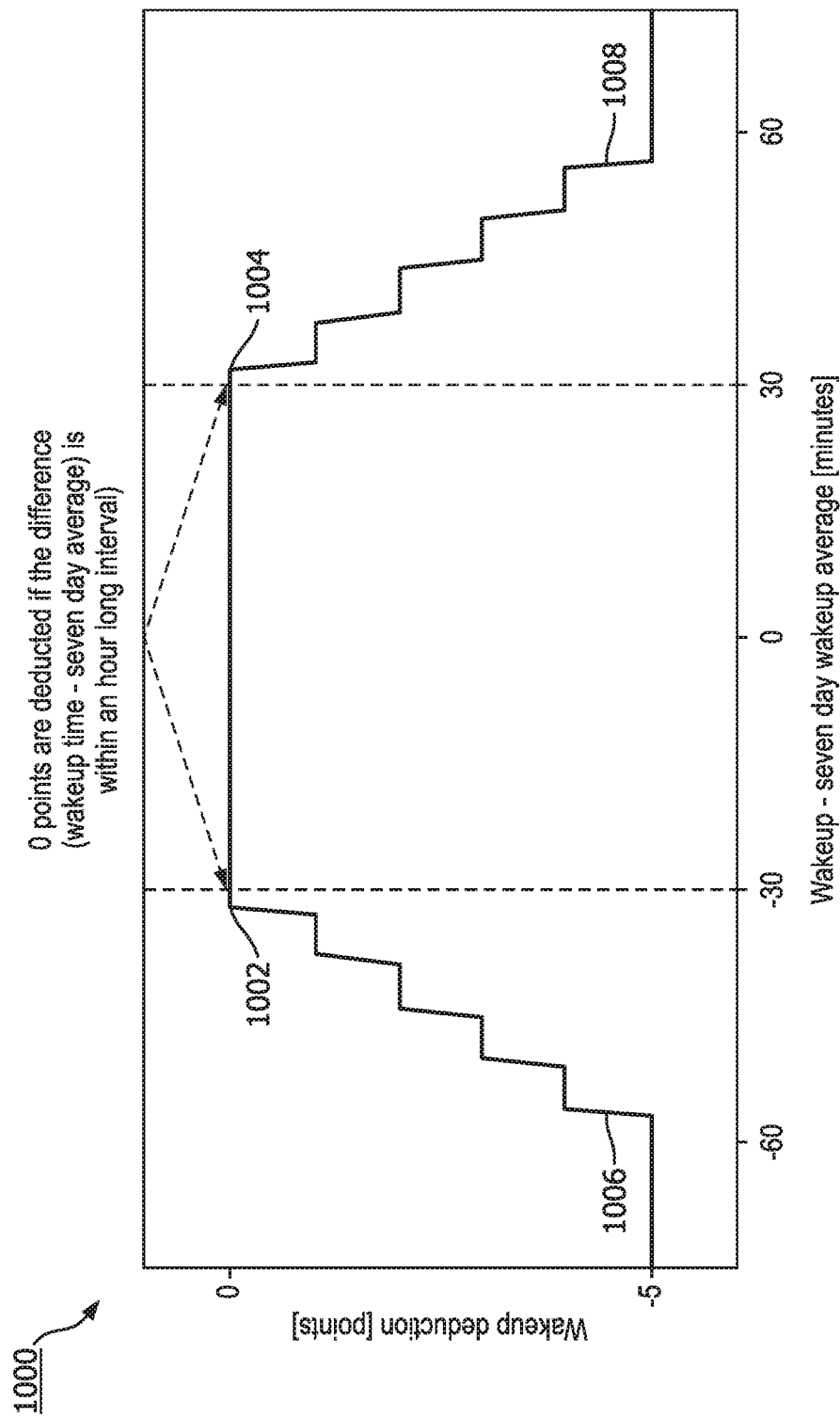
FIG. 10 is an illustrative diagram describing a relationship between wakeup time deviation and a corresponding sleep score point deduction, in accordance with various embodiments.

FIG. 10 is an illustrative diagram describing a relationship between wakeup time deviation and a corresponding sleep score point deduction, in accordance with various embodiments. FIG. 10 includes an illustrative graph 1000 of deductions applicable for computing a sleep session score based on an amount of deviation from an average wakeup time of the user, which relates to regularity factor 218. Similar to incentivizing a user to have a regular bedtime routine, regularity factor 218 may also be used to encourage and incentivize a user to have a regular wakeup time. If it is determined, based on data obtained from sensor(s) 108 of client device 110, that a user's wakeup time (e.g., a time when the user wakes from sleep) deviates from an average wakeup time, a deduction is applied. In one embodiment, the average wakeup time is determined based on a set of wakeup times for a given period of time. For example, the average wakeup time may be computed based on seven days of wakeup times, however other amounts of time can be used.

In one embodiment, if a detected wakeup time from a current sleep session is determined to be greater than or equal to a first threshold 1002 and less than or equal to a second threshold 1004, a deduction of 0 points will be applied for regularity factor 218. As an example, an amount of time between first threshold 1002 and second threshold 1004 may be one hour (e.g., 60 minutes). If the deviation from the average wakeup time for a given sleep session is less than threshold 1002 or greater than threshold 1004, then the deduction applied for factor 218 may be proportional to the deviation amount, as illustrated in graph 1000. In one embodiment, a maximum deduction amount may be applied if the deviation is less than or equal to threshold 1006 or greater than or equal to threshold 1008. For example, if the deviation from the average wakeup time exceeds one hour (e.g., 60 minutes) from the average wakeup time, then the maximum deduction amount may be applied for factor 218. In one embodiment, the maximum deduction applied for regularity factor 218 is a sleep-related parameter that can be optimized for a user based on data obtained from the plurality of sleep sessions. Furthermore, in one embodiment, the longest deviation from the average wakeup time with which the maximum deduction for factor 218 is to be applied is also a sleep-related parameter that can be optimized for a user based on data obtained from the plurality of sleep sessions.

In one embodiment, regularity factor 218 is computed based on both the deviation from the average bedtime and the deviation from the average wakeup time for a given sleep session. For instance, if a first deduction amount is determined for the deviation from the average bedtime and a second deduction amount is determined for the deviation from the average wakeup time, then both the first deduction amount and the second deduction amount can be used to compute the parameter value for regularity factor 218. As an example, the first deduction amount and the second deduction amount may be summed to obtain a total deduction amount to use for regularity factor 218 when computing a sleep session score. As another example, the first deduction amount and the second deduction amount may be averaged to obtain a deduction amount to use for regularity factor 218 when computing the sleep session score. As still yet another example, the first deduction amount and the second deduction amount may be weighted, and the weighted amounts may be combined, either linearly, quadratically, or via other known combinatory techniques.

Figure 11:
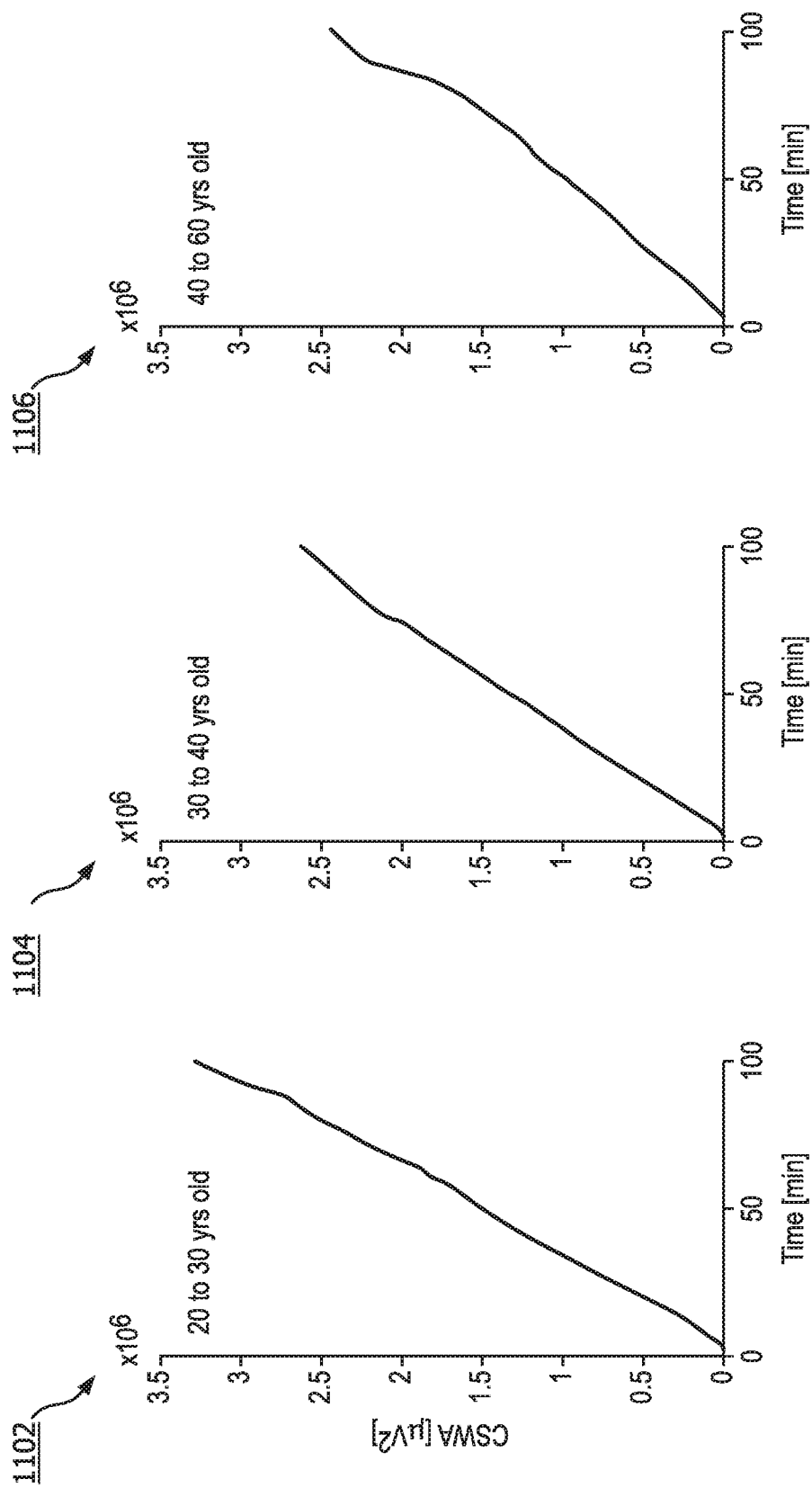
FIGS. 11A-C are illustrative diagrams describing a relationship between cumulative slow wave activity ("CSWA") and N3 sleep time for different age groups, in accordance with various embodiments.

FIGS. 11A-C are illustrative diagrams describing a relationship between cumulative slow wave activity ("CSWA") and N3 sleep time for different age groups, in accordance with various embodiments. FIGS. 11A-C include illustrative graphs 1102-1106, respectively, representative of a CSWA parameter for different age ranges. In one embodiment, interventions are capable of being provided to the user operating client device 110. For example, audible tones are capable of being provided using an auditory stimulation device. In one embodiment, the audible tones are provided via client device 110. In one embodiment, a dedicated intervention device capable of producing the audible tones is used. During EEG based detected non-rapid eye movement ("NREM") sleep, such audible tones are capable of being provided to enhance a restorative value of an individual's sleep by increasing an amplitude and amount of sleep slow waves, also referred to as delta waves, while not disturbing sleep. An amplitude and number of sleep slow waves correspond, in one embodiment, to slow wave activity ("SWA"), which corresponds to EEG power in the 0.5-4.0 Hz frequency band. A SWA accumulated over NREM sleep is useful, for example to quantify a restorative value of sleep that is provided.

In one embodiment, to determine an amount of bonus to be applied based on the intervention, a number of tones delivered, a ratio of detected NREM sleep/reference NREM sleep, and a ratio of the CSWA to a reference CSWA are all obtained. For instance, data obtained from sensor(s) 108 of client device 110, and/or a dedicated intervention device, indicates the number of tones deliver, the ratio of detected NREM sleep/reference NREM sleep, and a ratio of the CSWA to a reference CSWA. The ratio of detected NREM sleep to the reference NREM sleep, denoted by $\rho_{NREM}$, is determined using age based values stored by reference database 145 and detailed below in Table 5.

TABLE 9

| Age Range | NREM reference [minutes] |
|---|---|
| <30 | 86 |
| [30 to 40[ | 72 |
| ≥40 | 72 |

In one embodiment, the ratio of CSWA to a reference CSWA, denoted by $\rho_{SWA}$, is determined by dividing the CSWA associated with a current sleep session by the CSWA accumulated up and during the duration of the detected NREM for an age group associated with the user. As seen in FIGS. 11A-C, various example reference curves are shown for different age ranges. For instance, graph 1102 includes CSWA values for an age range of 20 to 30 year old individuals, graph 1104 includes CSWA values for an age range of 30 to 40 year old individuals, and graph 1106 includes CSWA values for an age range of 40 to 60 year old individuals. The information associated with graphs 1102, 1104, and 1106 are each stored by reference database 145 and accessed by computing system(s) 120 for determining a sleep score for the user for a given sleep session.

Figure 12:
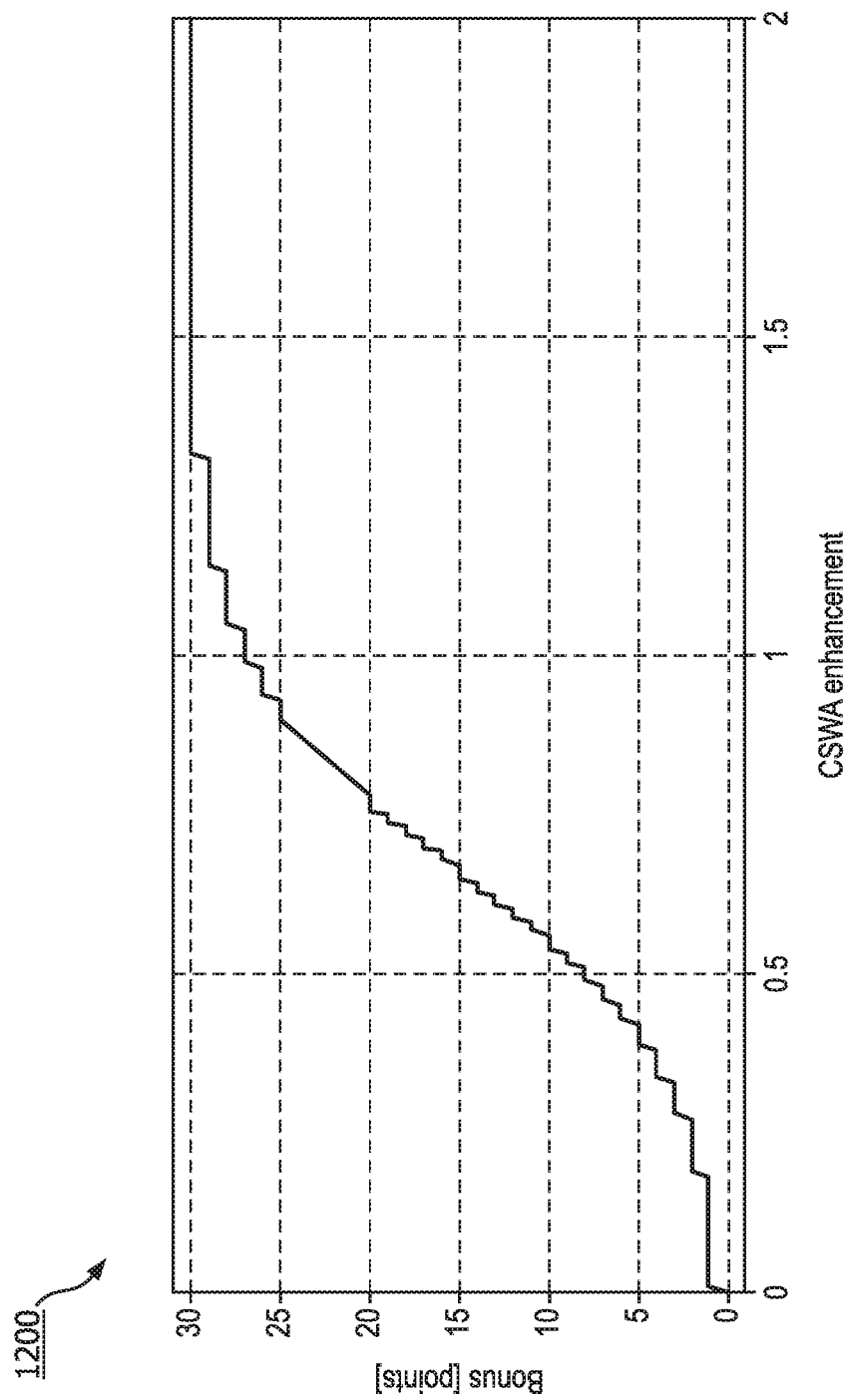
FIG. 12 is an illustrative diagram describing a relationship between a CSWA value and a corresponding sleep score bonus, in accordance with various embodiments.

FIG. 12 is an illustrative diagram describing a relationship between a CSWA value and a corresponding sleep score bonus, in accordance with various embodiments. FIG. 12 includes an illustrative graph 1200 indicating an amount of bonus applicable to the computed sleep score based on the determined CSWA value. In the illustrative embodiment, the CSWA amount is computed based on a product of the ratios $\rho_{NREM}$ and $\rho_{SWA}$. To determine the amount of bonus, a sigmoidal proportionality function is used that relates the determined CSWA amount for the user's age range to a bonus amount. In one embodiment, the maximum bonus may be a parameter that can be optimized based on data obtained from the plurality of sleep sessions. This parameter may be configurable and used for factor 220 when computing system(s) 120 determines the sleep score for a user for a given sleep session. As an example, the maximum value may be 30 points, which may be awarded as a bonus for the sleep score being calculated if the CSWA amount is greater than or equal to 1.5 μV. However, if the CSWA amount is less than 1.5 μV, the amount of bonus points is proportional to the CSWA score as described by graph 1200.

FIG. 13 is an illustrative diagram of an example interface displaying a sleep score and the computed values for a variety of sleep-related parameters used to determine the sleep score, in accordance with various embodiments. FIG. 13 is an illustrative diagram of an exemplary graphical user interface 1300 including a sleep session score and the various deductions applicable for each of factors 206-220. In the illustrative embodiment, graphical user interface 1300, which is capable of being displayed by I/O interface 112 (e.g., a display screen), includes an initial sleep session score value 1302 to which the deductions described above are applicable. For example, the initial sleep session score value may be set as 100.

In the illustrative embodiment, graphical user interface 1300 further includes a total sleep time deduction amount 1304, a sleep routine deduction amount 1306, a sleep latency deduction amount 1308, a time spent awake deduction amount 1310, a number of sleep interruptions deduction amount 1312, and a duration of N3 sleep deduction amount 1314. Additional deductions, such as for a duration of REM sleep and/or for deviation from an average sleep wakeup time, are also capable of being used. As an example, each of deductions 1304-1314 are less than or equal to zero in value such that, when applied to initial sleep session score value 1302, they reduce an amount of the sleep score.

A total base score 1316 is determine by adding each deduction 1304-1314 to initial sleep session score value 902. In this scenario, each deduction has a negative value (e.g., ≤0). Alternatively, each of deductions 1304-1314 is subtracted from initial sleep session score value 1302. In this scenario, each deduction is a positive value (e.g., ≥0). In one embodiment, one or more bonus values, stemming from one or more sleep interventions, are also applied to the base/initial sleep session score value 1302. The sleep interventions, as described above, positively impact a sleep session's score. For example, if deductions 1304-1314 are negative in that they reduce a sleep session score value, the bonus(es) 1318 is/are positive such that they increase the sleep session score value. A total sleep session score value 1320, accounting for any deductions and/or bonus identified for a particular user's sleep session, is then determined.

FIG. 14 is an illustrative diagram of the various sleep factors and the values of each sleep-related parameter used to generate an initial set of chromosome vectors, in accordance with various embodiments. Table 1400 of FIG. 14 includes a first column 1402 listing the various sleep-related factors that contribute to computing a sleep session score, as mentioned above in FIG. 2. For instance, the factors that contribute to a calculated sleep score include TST factor 206, WASO factor 208, SOL factor 210, number of sleep disruptions factor 212, N3 sleep duration factor 214, REM sleep duration factor 216, regularity factor 218 (e.g., deviation from average wakeup time and/or bedtime), and bonus factor 220.

Each of factors 206-220 include one or more sleep-related parameters listed within a column 1404 of Table 1400. In one embodiment, TST factor 206 includes a first sleep-related parameter 1406, a second sleep-related parameter 1408, and a third sleep-related parameter 1410. Details related to computing TST for a given sleep session are described above with reference to FIG. 3. In this embodiment, sleep-related parameter 1406 indicates a TST duration associated with a deduction of zero points; sleep-related parameter 1408 indicates a shortest possible TST duration; and sleep-related parameter 1410 indicates a maximum deduction amount associated with the shortest TST duration. In one embodiment, sleep-related parameter 1406 can initially be assigned one of three values: 300 minutes, 360 minutes, or 420 minutes (e.g., [300, 360, 420] minutes as seen in Table 1400). However, different values or ranges of values are capable of being used (e.g., [360, 420, 480] minutes; [270, 330, 390] minutes, [240, 300, 360, 420] minutes, etc.). In one embodiment, sleep-related parameter

1408 can initially be assigned one of three values: 60 minutes, 120 minutes, or 180 minutes (e.g., [60, 120, 180] minutes as seen in Table 1400). Similar to sleep-related parameter 1406, different values or ranges of values can be used (e.g., [60, 80, 100] minutes; [60, 100, 140] minutes; [30, 60, 90, 120] minutes, etc.). In one embodiment, sleep-related parameter 1410 can initially be assigned on of two values: 40 points or 50 points (e.g., [40, 50] points as seen in Table 1400). Different value ranges and different amounts of values for point deductions associated with the minimum TST can also be used such as, and without limitation, 41-50 (e.g., 10 point values), [45, 50] points, and [30, 40] points.

In one embodiment, WASO factor 208 includes a sleep-related parameter 1412. Details related to computing WASO for a given sleep session are described above with reference to FIG. 4. Sleep-related parameter 1412 is related to a maximum WASO deduction amount. In one embodiment, the maximum WASO deduction amount is assigned one of two values: 5 points or 10 points. However, different values, ranges of values, or number of values for the maximum WASO deduction amount can be used (e.g., [1, 10] points; [5, 10, 15] points).

In one embodiment, SOL factor 210 includes a sleep-related parameter 1414. Details related to computing WASO for a given sleep session are described above with reference to FIG. 5. Sleep-related parameter 1414 is related to a maximum SOL deduction amount. In one embodiment, the maximum SOL deduction amount is assigned one of two values: 5 points or 10 points. However, different values, ranges of values, or number of values for the maximum WASO deduction amount can be used (e.g., [1, 10] points; [5, 10, 15] points).

In one embodiment, sleep disruptions factor 212 includes a first sleep-related parameter 1416 and a second sleep-related parameter 1418. Details related to computing number of sleep disruptions for a given sleep session are described above with reference to FIG. 6. Sleep-related parameter 1416 is related to a maximum sleep interruption point deduction amount. Sleep-related parameter 1418 is related to a number of sleep interruptions that is considered to a maximum number of sleep interruptions. In one embodiment, the number of interruptions deduction amount for sleep-related parameter 1416 is assigned one of two values: 10 points or 20 points. However, different values, ranges of values, or number of values for the maximum WASO deduction amount can be used (e.g., [5, 25] points; [15, 25] points). In one embodiment, the number of interruptions deduction amount for sleep-related parameter 1418 is assigned one of two values: 5 interruptions or 10 interruption. However, different values, ranges of values, or number of values for the maximum WASO deduction amount can be used (e.g., [15, 20] points; [20, 30] points).

In one embodiment, N3 duration factor 214 includes a sleep-related parameter 1420. Details related to computing N3 duration for a given sleep session are described above with reference to FIG. 7. Sleep-related parameter 1420 is related to a maximum N3 deduction amount. In one embodiment, the maximum N3 deduction amount is assigned one of two values: 10 points or 20 points. However, different values, ranges of values, or number of values for the maximum N3 deduction amount can be used (e.g., [5, 20] points; [15, 20, 25] points).

In one embodiment, REM duration factor 216 includes a sleep-related parameter 1422. Details related to computing REM duration for a given sleep session are described above with reference to FIG. 8. Sleep-related parameter 1422 is related to a maximum REM deduction amount. In one embodiment, the maximum REM deduction amount is assigned one of two values: 10 points or 20 points. However, different values, ranges of values, or number of values for the maximum REM deduction amount can be used (e.g., [5, 20] points; [15, 20, 25] points).

In one embodiment, regularity factor 218 includes a first sleep-related parameter 1424 and a second sleep-related parameter 1426. Details related to computing number of regularity, e.g., deviation from average bedtime, deviation from average wakeup time, for a given sleep session are described above with reference to FIGS. 9 and 10. Sleep-related parameter 1424 is related to longest deviation from the average bedtime or wakeup time or both. In one embodiment, sleep-related parameter 1424 is determined based on an average of both the deviation from average bedtime and the deviation from average wakeup time. In another embodiment, sleep-related parameter 1424 is determined based on a weighted combination of both the deviation from average bedtime and the deviation from average wakeup time. Sleep-related parameter 1426 is related to maximum amount of points deducted for deviations from average bedtime and/or wakeup time. In one embodiment, the longest deviation from the average bedtime and/or wakeup time is assigned one of two values: 40 minutes or 60 minutes. However, different values, ranges of values, or number of values for the longest deviation time can be used (e.g., [30, 60] minutes; [45, 75] minutes). In one embodiment, the longest deviation point deduction amount for sleep-related parameter 1426 is assigned one of two values: 5 points or 10 points. However, different values, ranges of values, or number of values for the longest deviation point deduction amount can be used (e.g., [10, 20] points; [5, 25] points).

In one embodiment, bonus factor 220 includes a sleep-related parameter 1428. Details related to computing the bonus for a given sleep session are described above with reference to FIGS. 11 and 12. Sleep-related parameter 1428 is related to a maximum bonus amount. In one embodiment, the maximum bonus amount is assigned one of two values: 20 points or 30 points. However, different values, ranges of values, or number of values for the maximum REM deduction amount can be used (e.g., [10, 20] points; [20, 40] points).

Figure 15:
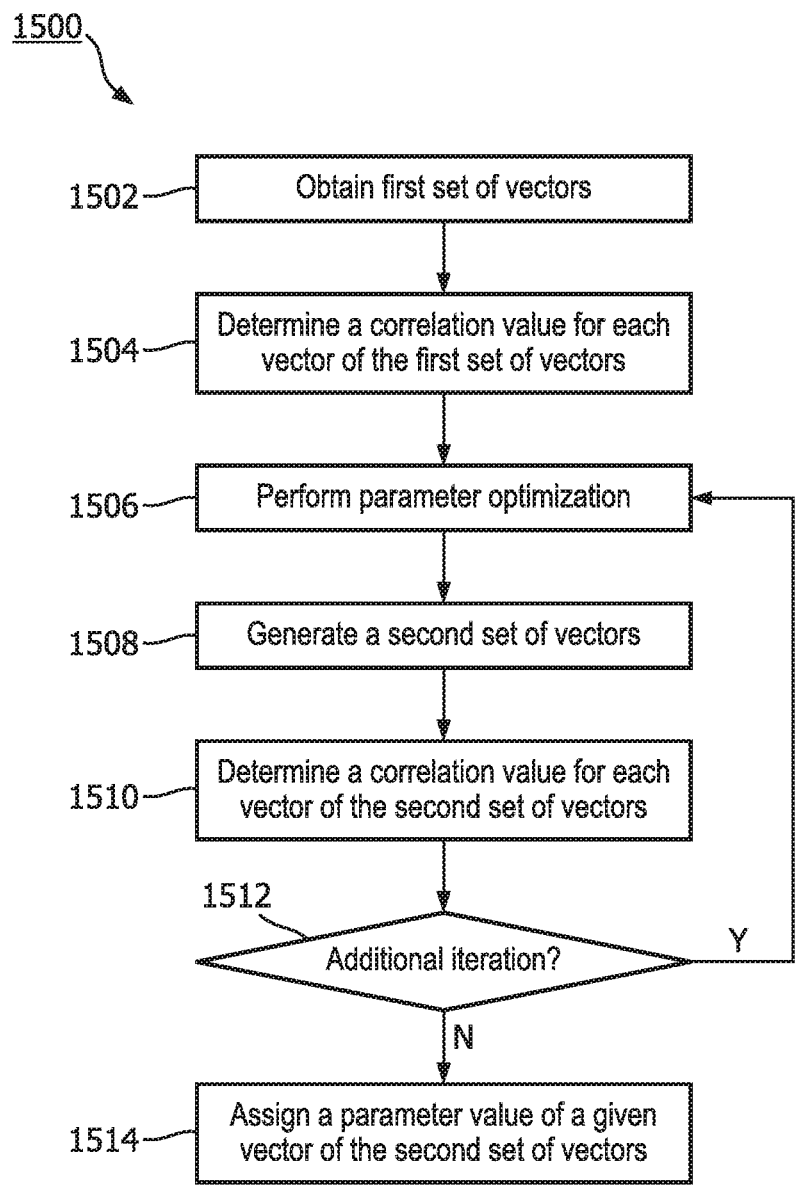
FIG. 15 is an illustrative flowchart of an exemplary process for assigning a parameter value to a vector based on correlation values determined for each vector of a set of chromosome vectors, in accordance with various embodiments.

FIG. 15 is an illustrative flowchart of an exemplary process for assigning a parameter value to a vector based on correlation values determined for each vector of a set of chromosome vectors, in accordance with various embodiments. In one embodiment, process 1500 of FIG. 15 begins at operation 1502. At operation 1502, a first set of vectors is obtained. In one embodiment, the first set of vectors is an initial set of vectors that span possible combinations of values for sleep-related parameters 1406-1428. For example, sleep-related parameters 1406 and 1408 include three values, while sleep-related parameters 1410-1428 include two values. In one embodiment, each parameter is represented by a nine-bit binary vector. In the illustrative embodiment, a nine-bit binary vector is selected because a largest parameter value, corresponding to total sleep time, is 480 minutes, and $(2\text{-bits})^9 = 512$ bits. However, different sized binary vectors may be used, such as 4-bit binary vectors or 8-bit binary vectors.

In one embodiment, the initial set of vectors includes 10,000 vectors, each being 108-bit binary vectors formed from the twelve nine-bit binary vectors associated with the twelve sleep-related parameters 1406-1428. In one embodiment, each 108-bit binary vector is referred to as a "chromosome," and is utilized to optimize a correlation between the calculated sleep score and a user-indicated sleep score.

The chromosome-vector, for example, may be used in a genetic algorithm, which is a type of optimization algorithm. The genetic algorithm allows for optimization algorithm that follows a similar process as that of natural selection. Furthermore, the genetic algorithm outputs, for the parameter values of each vector, integers as opposed to floating-point numbers. As mentioned above, integer numbers allow users to easily understand their sleep score and the deductions applied to generate their sleep score, as opposed to floating-point numbers which can cause confusion to users.

Each vector of the first set of vectors includes parameter values for sleep-related parameters 1406-1428. The parameter values are selected from the initial values illustrated in Table 1400 of FIG. 14. In one embodiment, the first set of vectors includes 10,000 chromosome vectors (e.g., 108-bit binary vectors). This initial population of vectors that form the initial, e.g., first, set of vectors stems from the number of values associated with each of the twelve sleep-related parameters 1406-1428. For example, sleep-related parameters 1406 and 1408 each include three values, as seen in FIG. 14 (e.g., parameter 1406 includes values [300, 360, 420] minutes; parameter 1408 includes values [60, 120, 180] minutes). Continuing this example, sleep-related parameters 1410-1428 each include two values, as seen in FIG. 14 (e.g., parameter 1410 includes values [40, 50] points; parameter 1412 includes values [5, 10] points; parameter 1414 includes values [5, 10] points; parameter 1416 includes values [10, 20] points; parameter 1418 includes values [5, 10] interruptions; parameter 1420 includes values [10, 20] points; parameter 1422 includes values [10, 20] points; parameter 1424 includes values [40, 60] minutes; parameter 1426 includes values [5, 10] points; and parameter 1428 includes values [20, 30] points). Therefore, the first set of vectors is composed of the product of two three-value parameters (e.g., $3^2$) and ten two-value parameters (e.g., $2^{10}$), which yields 9,096 values. For computational ease, an additional randomly chosen four values are repeated to reach 10,000 chromosome vectors. However, different amounts of vectors can be used to form the first set of vectors (e.g., 100, 1,000, 100,000, etc.), and the use of 10,000 vectors is not meant to be limiting. As an example, a first 108-bit binary vector, or chromosome vector $C_1$ may be notated as:

$C_1$=[$300_{9b}$, $60_{9b}$, $40_{9b}$, $5_{9b}$, $5_{9b}$, $10_{9b}$, $5_{9b}$, $10_{9b}$, $10_{9b}$, $40_{9b}$, $5_{9b}$, $20_{9b}$].

Here, each initial sleep-related parameter value is represented by a unique combination of nine-binary bits. For example, the first component of vector $C_1$, $300_{9b}$, is a nine-bit binary vector for an initial TST value of 300 minutes. In one embodiment, this vector is represented as [1, 0, 0, 1, 0, 1, 1, 0, 0], however this is exemplary and different representations are capable of being used.

In one embodiment, computing system(s) 120 generates the first set of 108-bit binary vectors. Alternatively, the first set of 108-bit binary vectors is generated by a separate chromosome vector generation system, which in turn provides the first set to computing system(s) 120. In one embodiment, the first set of vectors is stored in reference database 145, and accessed by computing system(s) 120 upon request for computing system(s) 120 to perform process 1500. In one embodiment, the first set of vectors is generated periodically such that, after a predetermined amount of time, the first set of vectors is discarded, and subsequently a new set of vectors is generated to replace the first set of vectors. The new set of vectors is then taken as being the "initial" set of vectors.

At operation 1504, a correlation value for each vector of the first set of vectors is determined. In one embodiment, upon generating the first set of vectors (e.g., by computing system(s) 120), or upon obtaining the first set of vectors (e.g., from reference database 145), correlation subsystem 122 is configured to determine a correlation value associated with each vector of the first set of vectors. The correlation value for the vector indicates an amount of correlation between the vector and a user-indicated sleep score, e.g., user-indicated sleep score, which is associated with a set of parameter values representative of a sleep metric of the user. In one embodiment, the user-indicated sleep score is obtained from user history database 140, and is determined by averaging a plurality of user-indicated sleep scores. For example, the user-indicated sleep score may be an average sleep score computing using one week, one month, one year, or other time period of user-provided sleep scores.

In one embodiment, correlation subsystem 122 determines a correlation value for each vector with respect to the user-indicated sleep score. For instance, correlation subsystem 122 performs a Pearson's correlation analysis for each vector from the set of vectors with the user-indicated sleep score. As mentioned above, each vector is representative of initial values for each of the twelve sleep-related parameter values. Based on the initial values for each of the twelve sleep-related parameter values, a possible sleep score is determined for that vector. Correlation subsystem 122 determines the possible sleep score associated with a given 108-bit binary vector (e.g., chromosome vector $C_1$), and performs the correlation analysis of that possible sleep score with the user-indicated sleep score. In one embodiment, the user-indicated sleep score is an average user-indicated sleep score determined based on a plurality of user-indicated sleep scores provided by the user for a period of time (e.g., one week, one month, etc.) In one embodiment, correlation subsystem 122 is configured to generate a plurality of correlation values, each corresponding to an estimated correlation of a possible sleep score given an initial set of sleep-related parameter values and the user-indicated sleep score. As an example, if the first set of vectors includes 10,000 108-bit binary vectors (e.g., chromosome vectors), then correlation subsystem 122 determines 10,000 correlation values (e.g., $r_1, r_2, \ldots, r_{10,000}$).

At operation 1506, an optimization for the first set of vectors is performed. In one embodiment, the optimization performed employs techniques of a genetic algorithm. However, additional correlation optimization techniques can alternatively or additionally be performed. Process 1600 of FIG. 16 describes one embodiment of the optimization process.

Figure 16:
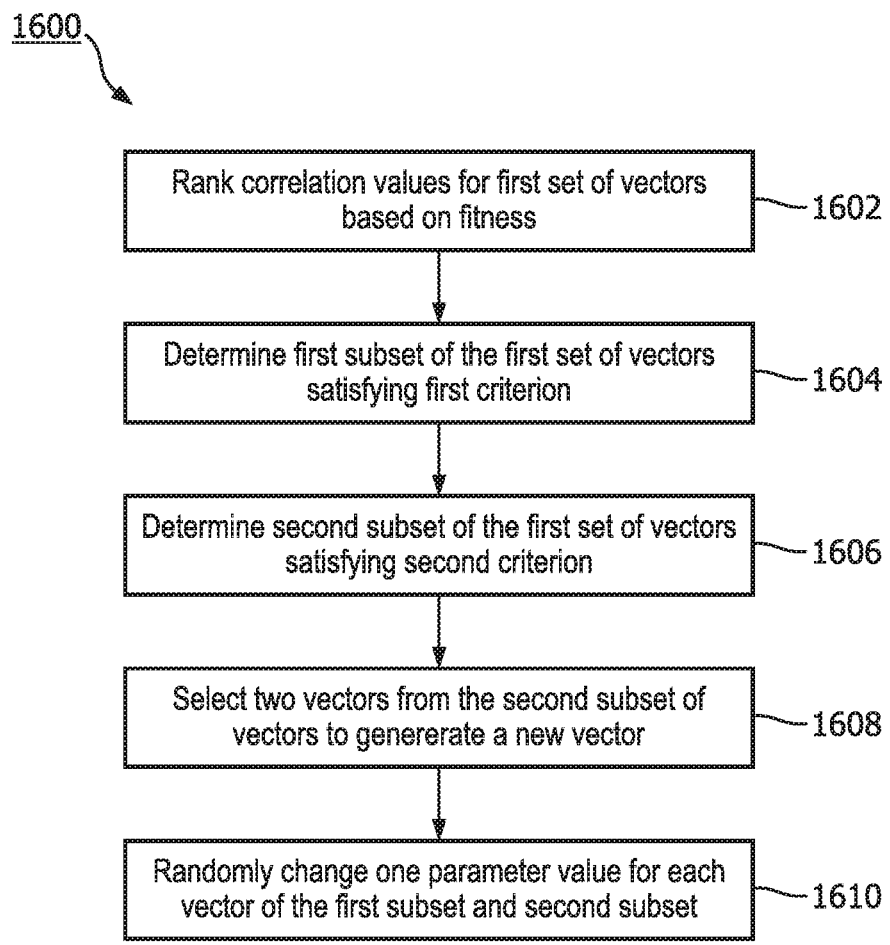
FIG. 16 is an illustrative flowchart of an exemplary process for generating a new set of chromosome vectors based on an initial set of chromosome vectors and correlation values with respect to a user's user-indicated sleep score, in accordance with various embodiments.

FIG. 16 is an illustrative flowchart of a process 1600 for generating a new set of chromosome vectors based on an initial set of chromosome vectors and correlation values with respect to a user's user-indicated sleep score, in accordance with various embodiments. In one embodiment, process 1600 begins at operation 1602. At operation 1602, correlation values for the first set of vectors are ranked. As mentioned previously, at operation 1504, correlation subsystem 122 determines a correlation value for each vector of the first set of vectors with respect to the user-indicated sleep score. After the correlation values are determined, correlation subsystem 122 provides the correlation values to optimization subsystem 124.

In one embodiment, optimization subsystem 124 ranks each of the correlation values from highest correlation (e.g., closest to 1) to lowest correlation (e.g., closest to −1). The closer the correlation value is to 1, the more well correlated that possible sleep score—determined based on the sleep-related parameter values used for a corresponding vector—is to the user-indicated sleep score provided by the user. In one embodiment, a fitness test of the correlation values is performed. The fitness value for a particular correlation value is determined, for example, using Equation 3:

$$f_i = \frac{r_i}{\sum_{j=1}^{10,000} r_j}.$$  Equation 3

In Equation 3, $f_i$ is the fitness value, and $r_i$, $r_j$ are the i-th and j-th correlation values, respectively. Although in Equation 3 the correlation values are summed from j=1 to j=10,000, if a different number of vectors is used to form the initial set of vectors, then the latter will differ. The fitness value is also referred to as a normalized correlation value. Therefore, in one embodiment, optimization system 124 is configured to rank the correlation values based on the fitness values.

At operation 1604, a first subset of the first set of vectors is determined. The first subset of vectors includes those vectors from the first set of vectors that satisfy a first criterion. In one embodiment, the first criterion corresponds to a top ten-percent most "fit" correlation values. For example, based on the ranked correlation values in terms of the fitness value associated therewith, the top ten percent of the fitness values are selected. The vectors from the first set of vectors associated with each of the fitness values of the top ten percent are identified, and those vectors are used to form the first subset of vectors. Although the top ten-percent most fit correlation values are selected to form the first subset of vectors, other percentages can be used such as, top five-percent most fit, top twenty-percent most fit, etc. In one embodiment, no top percent of the fitness values are used. In this scenario, operations 1604 and 1606 are skipped, and process 1600 proceeds to operation 1608.

At operation 1606, a second subset of the first set of vectors is determined. The second subset of vectors includes those vectors from the first set of vectors that satisfy a second criterion. In one embodiment, the second criterion corresponds to a next ninety percent correlation/fitness values. In other words, the second subset of vectors includes all of the vectors from the first set of vectors that are not included within the first subset of vectors, and thus have a fitness value that is not within the top ten percent of the correlation/fitness values based on the rank.

At operation 1608, two vectors from the second subset of vectors are selected, and a new vector is generated using those two vectors. The new vector may be referred to as a "child" vector, and the two vectors may be referred to as "parent" vectors. In one embodiment, a first 108-bit binary vector from the first set of vectors having a correlation value not of the top ten-percent most "fit" correlation values and a second 108-bit binary vector from the first set of vectors also having a correlation value not of the top ten-percent most "fit" correlation values are selected randomly. In one embodiment, the first vector and the second vector are selected from a group of vectors from the second subset based on the fitness level. For example, if the second subset of vectors includes 9,000 vectors, an intermediate set of vectors is randomly selected from the 9,000 vectors based on the fitness value associated therewith. For instance, a vector having a very low fitness level has a greater likelihood of being selected than a vector having a higher fitness level (that is still not within the top 10%). In one embodiment, from this group of vectors from the second subset of vectors, a cross-over process is performed by which child vectors are generated.

From the first vector and the second vector, the new vector is generated. The new vector is constructed by randomly selecting one of the parameter values from the first vector and the second vector for each of the sleep-related parameters. For example, if for parameter 1406, the first vector has value A and the second vector has value B, then optimization subsystem 124 randomly selects one of A or B to assign as the parameter value for parameter 1406 of the new vector. Depending on the number of vectors included within the group of vectors randomly selected from the second subset of vectors, the number of child vectors will vary. For example, if the second subset of vectors includes 9,000 vectors, and the group of vectors selected randomly for cross-over processing includes 5,000 pairs of vectors, then optimization system 124 will generate 5,000 child vectors. For instance, for 5,000 randomly selected "couples" (e.g., two vectors from the second subset of vectors), two "child" vectors are generated by recombination of the parameter values from each of the two "parent" vectors of that couple.

At operation 1610, one parameter of each sleep-related parameter is randomly changed for each vector of the second set of vectors (e.g., the first subset and the second subset of vectors). Randomly changing the parameter value may be referred to as a "mutation," and is one aspect of the genetic algorithm. In one embodiment, the random change of the parameter value (e.g., mutation) is a flip of one binary bit of a 108-bit binary vector from either 0 to 1 or from 1 to 0. The mutation is applied at a predefined probability, such as 1%. In one embodiment, the mutation is applied to all of the vectors, e.g., the first subset of vectors and each of the child vectors generated from the second subset of vectors.

Returning to process 1500, at operation 1508, a second set of vectors is generated. The second set of vectors may be the vectors produced by process 1600 of FIG. 16. For instance, as a result of process 1600, a new "population" of vectors, which is referred to as the second set of vectors, is generated.

At operation 1510, a correlation value for each vector of the second set of vectors is determined. For example, a Pearson's correlation analysis is performed for each vector of the second set of vectors with respect to the user-indicated sleep score. In one embodiment, correlation subsystem 122 is employed to perform the correlation analysis of the second subset of vectors. After the correlation values, e.g., for each vector of the second set of vectors, are determined, process 1500 proceeds to operation 1512.

At operation 1512, a determination is made as to whether an additional iteration of process 1600 is needed to generate a new set of vectors. In one embodiment, optimization subsystem 124 is configured such that process 1600 is iterated a predetermined number of times. For example, process 1600 may be repeated 10,000 times, 100,000 times, or 1,000,000 times. After each iteration, the average correlation value of the set of newly generated vectors is compared with a threshold correlation value. If the average correlation value satisfies a correlation criterion, then process 1500 proceeds to operation 1514. At operation 1514, a parameter value of a given vector of the second set of vectors is assigned. In one embodiment, in response to determining that the average correlation value satisfies the correlation criterion, a given vector of the second set of vectors is selected. The given vector may be selected based on the given vector having a largest correlation value with respect to the correlation values associated with the second set of vectors. In other words, the given vector is selected because an associated sleep score computed using the sleep-related parameter values for that vector is best correlated to the user-indicated sleep score. However, if the average correlation does not satisfy the correlation criterion, then process 1500 returns to operation 1506.

In one embodiment, the correlation criterion is a value, and the average correlation value satisfies the correlation criterion if greater than or equal to that value. For example, the value may be 0.01. Alternatively, the correlation value satisfies the correlation criterion if less than or equal to the value.

If the correlation criteria is not satisfied, then a new set of vectors may be generated. In one embodiment, the new set of vectors is generated by performing process 1600 again to obtain the new set of vectors. Thus, an additional iteration of process 1600, e.g., generating vectors, determining correlation values, etc., occurs. After the new set of vectors is generated, a determination is made as an average correlation value associated with the new set of vectors satisfies the correlation criterion. If so, then no additional iterations are needed, and process 1500 proceeds to operation 1514. However, if the new average correlation value still does not satisfy the correlation criterion, then another iteration occurs. The iterations will continue until a new set of vectors is generated that result in a correlation value satisfying the correlation criterion. In one embodiment, the second set of vectors of operation 1508 is the resulting set of vectors generated after the iterations have been completed and the correlation values indicate that additional iterations are not needed.

In one embodiment, extraction subsystem 126 is configured to extract the new sleep-related parameter values for each sleep-related parameter based on the vector identified at operation 1514. The new sleep-related parameter values are considered to be optimized for the user based on the data obtained from the user's sleep sessions. For example, if the vector identified at operation 1514 is formed by a first set of sleep-related parameter values, then each sleep-related parameter value from this vector is extracted by extraction system 126. The extracted sleep-related parameters are then stored, in one embodiment, in reference database 145 and/or user history database 140. Thus, for subsequent sleep score computations by computing system(s) 120, the newly extracted sleep-related parameter values are used in conjunction with determining each of factors 206-212.

In one embodiment, the set of newly generated vectors is stored by reference database 145. Therefore, if at a later time an optimization of the sleep-related parameter values is to be performed, the previously generated set of vectors are used as the initial set of vectors for process 1500. By doing so, computing system(s) 120 allows for the sleep score computations to evolve and adapt with a particular user.

In one embodiment, the use of chromosome vectors allows for the output sleep score calculated by computing system(s) 120 to be an integer value. Furthermore, use of chromosome vectors allows the breakdown of each sleep factor to also be represented as an integer value. Therefore, when presenting a user with their calculated sleep score, as seen in FIG. 13, the score and the deductions are each shown as integers. This provides a user with an easier ability to understand their sleep score and further how their sleep score was calculated. In contrast, use of floating-point numbers can cause confusion to users as it can be difficult to understand how different floating point deductions impact the calculated sleep score. Thus, the techniques described herein not only allow for improved sleep-related parameters to be computed that are dynamic, and user centric, but also allows for subsequent sleep scores that are computed to be clearer and easier for a user to understand.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system for optimizing a plurality of sleep-related parameters to be used for calculating a sleep score, the system comprising:
  a memory; and
  one or more processors configured by machine-readable instructions stored by the memory to:
   obtain a first set of vectors, wherein each vector of the first set of vectors comprises first parameter values for the sleep-related parameters, wherein each vector of the first set of vectors comprises a chromosome binary vector generated based on the sleep-related parameters, and wherein the sleep-related parameters include one or more of a sleep architecture parameter, a sleep continuity parameter, a sleep onset parameter or a sleep wakeup time parameter;
   for each vector of the first set of vectors, determine a correlation value associated with the vector, the correlation value for the vector indicating an amount of a correlation between the vector and a subjective user-indicated sleep score associated with a set of second parameter values representative of a sleep metric of the user;
   generate a second set of vectors including: (i) a first subset of the first set of vectors having correlation values that satisfy a first criterion, and (ii) a second subset of the first set of vectors having correlation values that satisfy a second criterion, wherein the one or more processors are further configured by the machine-readable instructions to determine a rank of the correlation values associated with the first set of vectors, wherein the first criterion corresponds to a first percent of the correlation values based on the rank of the correlation values, and wherein the second criterion corresponds to a second percent of the correlation values based on the rank of the correlation values;
   for each vector of the second set of vectors, determine a correlation value associated with the vector, wherein the correlation value for the vector indicates an amount of a correlation between the vector and the subjective user-indicated sleep score; and for each parameter of the plurality of sleep-related parameters, assign a third parameter value comprising a given vector of the second set of vectors to the parameter based on the correlation values associated with the second set of vectors, wherein the given vector of the second set of vectors is selected based on the given vector being associated with a correlation value indicating a greatest amount of correlation with respect to the user-indicated sleep score relative to correlation values associated with other vectors of the second set of vectors.

2. The system of claim 1, wherein the one or more processors are further configured by the machine-readable instructions to:

generate the first set of vectors, wherein each vector of the first set of vectors is generated by selecting the first parameter value for each parameter of the sleep-related parameters from a range of possible parameter values associated with the parameter of the sleep-related parameters, wherein:
  a computed associated sleep score is determined for the vector based on the selected parameter values, and
  the correlation value for the vector is determined based on the associated sleep score.

3. The system of claim 1, wherein the one or more processors are further configured by the machine readable instructions to:

obtain the subjective user-indicated sleep score indicative of a user rating reflecting a quality of a sleep session of a user, wherein the user-indicated sleep score is determined based on a plurality of user ratings provided by the user over a period of time.

4. The system of claim 1, wherein the second set of vectors being generated further comprises the one or more processors being configured by the machine-readable instructions to:

select two vectors from the second subset of the first set of vectors; and generate a new vector by randomly selecting one of the parameter values from the two vectors for each of the sleep-related parameters.

5. The system of claim 4, wherein the one or more processors are further configured by the machine-readable instructions to:

for each vector of the second set of vectors, randomly change one parameter value of each sleep-related parameter for the vector.

6. The system of claim 1, wherein the one or more processors are further configured by the machine-readable instructions to:

determine an average correlation value based on the determined correlation values; and in response to the average correlation value satisfying a threshold correlation criterion, select the given vector of the second set of vectors based on the given vector having a largest correlation value with respect to the correlation values associated with the second set of vectors.

7. The system of claim 1, wherein the one or more processors are further configured by the machine-readable instructions to:

determine an average correlation value based on the correlation value associated with each vector of the second set of vectors; and in response to the average correlation value not satisfying a threshold correlation criterion, cause a new set of vectors to be generated by iteratively generating vectors and determining correlation values associated with the vectors until the correlation criterion is satisfied.

8. A system configured to optimize a plurality of sleep-related parameters to be used for calculating a sleep score, the system comprising:

means configured to obtain a first set of vectors, wherein each vector of the first set of vectors comprises first parameter values for the sleep-related parameters, wherein each vector of the first set of vectors comprises a chromosome binary vector generated based on the sleep-related parameters, and wherein the sleep-related parameters include one or more of a sleep architecture parameter, a sleep continuity parameter, a sleep onset parameter or a sleep wakeup time parameter;

means configured to determine, for each vector of the first set of vectors, a correlation value associated with the vector, the correlation value for the vector indicating an amount of a correlation between the vector and a subjective user-indicated sleep score associated with a set of second parameter values representative of a sleep metric of the user;

means configured to generate a second set of vectors including: (i) a first subset of the first set of vectors having correlation values that satisfy a first criterion, and (ii) a second subset of the first set of vectors having correlation values that satisfy a second criterion, and means configured for determining a rank of the correlation values associated with the first set of vectors, wherein the first criterion corresponds to a first percent of the correlation values based on the rank of the correlation values, and wherein the second criterion corresponds to a second percent of the correlation values based on the rank of the correlation values;

means configured to determine, for each vector of the second set of vectors, a correlation value associated with the vector, wherein the correlation value for the vector indicates an amount of a correlation between the vector and the subjective user-indicated sleep score; and means configured to assign, for each parameter of the plurality of sleep-related parameters, a third parameter value comprising a given vector of the second set of vectors to the parameter based on the correlation values associated with the second set of vectors, and means configured to select the given vector of the second set of vectors based on the given vector being associated with a correlation value indicating a greatest amount of correlation with respect to the user-indicated sleep score relative to correlation values associated with other vectors of the second set of vectors.

\* \* \* \* \*